(12) United States Patent
Williams et al.

(10) Patent No.: US 11,298,174 B2
(45) Date of Patent: *Apr. 12, 2022

(54) CRYOGENIC ABLATION SYSTEM AND METHOD

(71) Applicant: Pentax of America, Inc., Montvale, NJ (US)

(72) Inventors: Richard S. Williams, Redwood City, CA (US); Peter Garcia-Meza, San Francisco, CA (US)

(73) Assignee: Pentax of America, Inc., Montvale, NJ (US)

( * ) Notice: Subject to any disclaimer, the term of this patent is extended or adjusted under 35 U.S.C. 154(b) by 316 days.

This patent is subject to a terminal disclaimer.

(21) Appl. No.: 16/508,165

(22) Filed: Jul. 10, 2019

(65) Prior Publication Data

US 2019/0328438 A1 Oct. 31, 2019

Related U.S. Application Data

(60) Continuation of application No. 14/876,035, filed on Oct. 6, 2015, now Pat. No. 10,383,676, which is a
(Continued)

(51) Int. Cl.
*A61B 18/02* (2006.01)
*A61M 25/10* (2013.01)
(Continued)

(52) U.S. Cl.
CPC ......... *A61B 18/02* (2013.01); *A61M 25/1034* (2013.01); *A61M 25/10185* (2013.11);
(Continued)

(58) Field of Classification Search
CPC ........... A61B 18/02; A61B 2018/0022; A61B 2018/00488; A61B 2018/00714;
(Continued)

(56) References Cited

U.S. PATENT DOCUMENTS

| 4,333,452 A | 6/1982 | Au |
| 4,924,862 A | 5/1990 | Levinson |

(Continued)

FOREIGN PATENT DOCUMENTS

| CN | 101584602 A | 11/2009 |
| CN | 101972513 A | 2/2011 |

(Continued)

OTHER PUBLICATIONS

U.S. Appl. No. 12/611,057—Notice of Allowance dated Nov. 5, 2012, 11 pages.

(Continued)

*Primary Examiner* — Khadijeh A Vahdat
(74) *Attorney, Agent, or Firm* — Haynes Beffel & Wolfeld LLP; Andrew Dunlap

(57) ABSTRACT

A device for treating esophageal target tissue comprises a catheter, a balloon and a refrigerant delivery device. The catheter has a distal portion and a refrigerant delivery lumen. The balloon is mounted to and the refrigerant delivery device is coupled to the distal portion. The refrigerant delivery device comprises a chamber with the refrigerant delivery lumen opening into the chamber, a refrigerant delivery opening fluidly coupled to the balloon interior, and a distribution passageway fluidly coupling the chamber and the refrigerant delivery opening. A refrigerant is deliverable through the refrigerant delivery lumen, into the chamber, through the distribution passageway, through the refrigerant delivery opening and into the balloon interior so to place the balloon into an expanded, cooled state so that the balloon can press against and cool esophageal target tissue. The medical device may include means for sensing a leak in the balloon.

18 Claims, 24 Drawing Sheets

Related U.S. Application Data continuation of application No. 13/766,567, filed on Feb. 13, 2013, now Pat. No. 9,168,081, which is a division of application No. 12/611,057, filed on Nov. 2, 2009, now Pat. No. 8,382,746.

(60) Provisional application No. 61/116,991, filed on Nov. 21, 2008.

(51) Int. Cl.
*A61B 17/22* (2006.01)
*A61B 18/00* (2006.01)

(52) U.S. Cl.
CPC ............ *A61B 2017/22051* (2013.01); *A61B 2018/0022* (2013.01); *A61B 2018/00488* (2013.01); *A61B 2018/00714* (2013.01); *A61B 2018/0212* (2013.01); *A61B 2018/0262* (2013.01); *A61B 2018/0268* (2013.01); *A61M 2025/1084* (2013.01); *A61M 2210/105* (2013.01); *Y10T 29/49826* (2015.01)

(58) Field of Classification Search
CPC .... A61B 2018/0212; A61B 2018/0262; A61B 2018/0268; A61B 2017/22051; A61M 2025/1084; A61M 2210/105; A61M 25/10185; A61M 25/1034; Y10T 29/49826
USPC ...................................... 606/21–26
See application file for complete search history.

(56) References Cited

U.S. PATENT DOCUMENTS

| | | | |
|---|---|---|---|
| 5,035,705 A | 7/1991 | Burns |
| 5,342,301 A | 8/1994 | Saab |
| 5,868,735 A | 2/1999 | Lafontaine |
| 5,971,979 A | 10/1999 | Joye et al. |
| 6,027,499 A | 2/2000 | Johnston et al. |
| 6,283,959 B1 | 9/2001 | Lalonde et al. |
| 6,355,029 B1 | 3/2002 | Joye et al. |
| 6,383,181 B1 | 5/2002 | Johnston et al. |
| 6,383,203 B1 | 5/2002 | Makihara |
| 6,428,534 B1 | 8/2002 | Joye et al. |
| 6,443,947 B1 | 9/2002 | Marko et al. |
| 6,468,297 B1 | 10/2002 | Williams et al. |
| 6,514,245 B1 | 2/2003 | Williams et al. |
| 6,537,271 B1 | 3/2003 | Murray et al. |
| 6,551,274 B2 | 4/2003 | Heiner |
| 6,626,861 B1 | 9/2003 | Hart et al. |
| 6,648,878 B2 | 11/2003 | Lafontaine |
| 6,666,858 B2 | 12/2003 | Lafontaine |
| 6,709,431 B2 | 3/2004 | Lafontaine |
| 6,746,465 B2 | 6/2004 | Diederich et al. |
| 6,786,901 B2 | 9/2004 | Joye et al. |
| 6,875,209 B2 | 4/2005 | Zvuloni et al. |
| 6,905,510 B2 | 6/2005 | Saab |
| 6,908,462 B2 | 6/2005 | Joye et al. |
| 6,929,639 B2 | 8/2005 | Lafontaine |
| 6,953,469 B2 | 10/2005 | Ryan |
| 7,022,120 B2 | 4/2006 | Lafontaine |
| 7,025,762 B2 | 4/2006 | Johnston et al. |
| 7,156,860 B2 | 1/2007 | Wallsten et al. |
| 7,220,257 B1 | 5/2007 | Lafontaine |
| 7,727,228 B2 | 6/2010 | Abboud et al. |
| 8,038,598 B2 | 10/2011 | Khachi |
| 8,172,747 B2 | 5/2012 | Wallace et al. |
| 8,382,746 B2 | 2/2013 | Williams et al. |
| 8,409,266 B2 | 4/2013 | Lafontaine |
| 8,740,895 B2 | 6/2014 | Mayse et al. |
| 9,017,324 B2 | 4/2015 | Mayse et al. |
| 9,050,073 B2 | 6/2015 | Newell et al. |
| 9,168,081 B2 | 10/2015 | Williams et al. |
| 9,414,878 B1 | 8/2016 | Wu et al. |
| 2002/0007179 A1 | 1/2002 | Dobak et al. |
| 2002/0010460 A1 | 1/2002 | Joye et al. |
| 2002/0026182 A1 | 2/2002 | Joye et al. |
| 2002/0062122 A1 | 5/2002 | Lehmann et al. |
| 2003/0060762 A1 | 3/2003 | Zvuloni et al. |
| 2003/0060813 A1 | 3/2003 | Loeb et al. |
| 2003/0088240 A1 | 5/2003 | Saadat |
| 2004/0147811 A1 | 7/2004 | Diederich et al. |
| 2004/0210281 A1 | 10/2004 | Dzeng et al. |
| 2004/0215296 A1 | 10/2004 | Ganz et al. |
| 2004/0243119 A1 | 12/2004 | Lane et al. |
| 2005/0137619 A1 | 6/2005 | Schewe et al. |
| 2005/0209587 A1 | 9/2005 | Joye et al. |
| 2005/0245943 A1 | 11/2005 | Zvuloni et al. |
| 2006/0030843 A1 | 2/2006 | Lane et al. |
| 2006/0041256 A1 | 2/2006 | Edwards et al. |
| 2006/0086362 A1 | 4/2006 | Solomon |
| 2006/0259029 A1 | 11/2006 | Utley et al. |
| 2007/0066962 A1 | 3/2007 | Rutter |
| 2007/0250050 A1 | 10/2007 | Lafontaine |
| 2007/0299433 A1 | 12/2007 | Williams et al. |
| 2007/0299443 A1 | 12/2007 | DiPoto et al. |
| 2008/0262476 A1 | 10/2008 | Krause et al. |
| 2008/0312644 A1 | 12/2008 | Fourkas et al. |
| 2009/0099638 A1 | 4/2009 | Grewe |
| 2009/0099639 A1 | 4/2009 | Sabaria |
| 2009/0118723 A1 | 5/2009 | Lalonde et al. |
| 2009/0182317 A1 | 7/2009 | Bencini |
| 2009/0209949 A1 | 8/2009 | Ingle et al. |
| 2009/0234345 A1 | 9/2009 | Hon |
| 2010/0130970 A1 | 5/2010 | Williams et al. |
| 2010/0249601 A1 | 9/2010 | Courtney |
| 2011/0184398 A1 | 7/2011 | Desrochers |
| 2012/0101485 A1 | 4/2012 | Wittenberger |
| 2012/0130458 A1 | 5/2012 | Ryba et al. |
| 2012/0143177 A1 | 6/2012 | Avitall |
| 2012/0172072 A1 | 7/2012 | Baxter et al. |
| 2012/0197245 A1 | 8/2012 | Burnett et al. |
| 2013/0012772 A1 | 1/2013 | Gunday et al. |
| 2013/0018366 A1 | 1/2013 | Wu et al. |
| 2013/0023770 A1 | 1/2013 | Courtney et al. |
| 2013/0030425 A1 | 1/2013 | Stewart et al. |
| 2013/0110100 A1 | 5/2013 | Groves et al. |
| 2013/0197500 A1 | 8/2013 | Williams et al. |
| 2013/0231650 A1 | 9/2013 | Watson |
| 2013/0231651 A1 | 9/2013 | Burr et al. |
| 2013/0253491 A1 | 9/2013 | Burr et al. |
| 2013/0289549 A1 | 10/2013 | Nash et al. |
| 2013/0304061 A1 | 11/2013 | Chang et al. |
| 2013/0345688 A1 | 12/2013 | Babkin et al. |
| 2015/0045826 A1 | 2/2015 | Drasler et al. |
| 2015/0126985 A1 | 5/2015 | Newell et al. |
| 2015/0190036 A1 | 7/2015 | Saadat |
| 2015/0196345 A1 | 7/2015 | Newell et al. |
| 2015/0230700 A1 | 8/2015 | Chandler et al. |
| 2015/0265329 A1 | 9/2015 | Lalonde et al. |
| 2015/0342660 A1 | 12/2015 | Nash |
| 2016/0066975 A1 | 3/2016 | Fourkas et al. |
| 2016/0302841 A1 | 10/2016 | Williams et al. |

FOREIGN PATENT DOCUMENTS

| | | |
|---|---|---|
| CN | 102223848 A | 10/2011 |
| CN | 102639077 A | 8/2012 |
| CN | 102715950 A | 10/2012 |
| CN | 102883659 A | 1/2013 |
| CN | 103200891 A | 7/2013 |
| CN | 103930153 A | 7/2014 |
| CN | 104244854 A | 12/2014 |
| CN | 104271064 A | 1/2015 |
| CN | 105705108 B | 12/2017 |
| EP | 0925045 A1 | 6/1999 |
| EP | 1199053 A1 | 4/2002 |
| EP | 1547537 A1 | 6/2005 |
| JP | 2000504967 A | 4/2000 |
| JP | 2000516696 A | 12/2000 |
| JP | 2001511690 A | 8/2001 |
| JP | 2001524345 A | 12/2001 |
| JP | 2004516042 A | 6/2004 |

(56) References Cited

FOREIGN PATENT DOCUMENTS

| | | | |
|---|---|---|---|
| JP | 2005503241 A | 2/2005 |
| JP | 2008000553 A | 1/2008 |
| JP | 1117958 B2 | 7/2008 |
| JP | 2008523897 A | 7/2008 |
| JP | 2008245954 A | 10/2008 |
| JP | 2012509146 A | 4/2012 |
| JP | 2015-509791 A | 4/2015 |
| JP | 6402317 B2 | 10/2018 |
| WO | 9804221 A1 | 2/1998 |
| WO | 9836783 A1 | 8/1998 |
| WO | 9927862 A1 | 6/1999 |
| WO | 9955401 A1 | 11/1999 |
| WO | 03026719 A2 | 4/2003 |
| WO | 2008042890 A1 | 4/2008 |
| WO | 2010059519 A1 | 5/2010 |
| WO | 2010078175 A1 | 7/2010 |
| WO | 2012162829 A1 | 12/2012 |
| WO | 2013110156 A1 | 8/2013 |
| WO | 2013163325 A2 | 10/2013 |
| WO | 2014026055 A1 | 2/2014 |
| WO | 2014089380 A2 | 6/2014 |
| WO | 2014137383 A1 | 9/2014 |
| WO | 2015066521 A1 | 5/2015 |
| WO | 2015188013 A1 | 12/2015 |
| WO | 2016025964 A1 | 2/2016 |
| WO | 2016186964 A1 | 11/2016 |
| WO | 2017200877 A1 | 11/2017 |

OTHER PUBLICATIONS

U.S. Appl. No. 12/611,057—Office Action dated Jun. 19, 2012, 22 pages.
U.S. Appl. No. 12/611,057—Response to Office Action dated Jun. 19, 2012 filed Oct. 18, 2012, 22 pages.
U.S. Appl. No. 12/611,057—Response to Restriction Requirement dated Apr. 28, 2012 filed May 24, 2012, 11 pages.
U.S. Appl. No. 12/611,057—Restriction Requirement dated Apr. 27, 2012, 11 pages.
U.S. Appl. No. 13/766,567—Notice of Allowance dated Jun. 22, 2015, 9 pages.
U.S. Appl. No. 13/766,567—Office Action dated Dec.1, 2014, 10 pages.
U.S. Appl. No. 13/766,567—Office Action dated Mar. 12, 2014, 9 pages.
U.S. Appl. No. 13/766,567—Response to Office Action dated Dec. 1, 2014 filed Feb. 11, 2015, 8 pages.
U.S. Appl. No. 13/766,567—Response to Office Action dated Mar. 12, 2014, filed Sep. 4, 2014, 9 pages.
U.S. Appl. No. 13/766,567—Response to Restriction Requirement dated Nov. 19, 2013, filed Dec. 11, 2013, 6 pages.
U.S. Appl. No. 13/766,567—Restriction Requirement dated Nov. 19, 2013, 11 pages.
U.S. Appl. No. 14/876,035—Office Action dated May 29, 2018, 9 pages.
U.S. Appl. No. 14/876,035—Response to Office Action dated May 28, 2018, filed Aug. 21, 2019, 7 pages.
U.S. Appl. No. 14/876,035—Final Office Action dated Jan. 4, 2019, 8 pages.
U.S. Appl. No. 14/876,035—Response to Final Office Action dated Jan. 4, 2019, filed Mar. 1, 2019, 5 pages.
U.S. Appl. No. 14/876,035—Notice of Allowance dated Apr. 9, 2019, 8 pages.
U.S. Appl. No. 14/714,101, filed May 15, 2015, U.S. Pat. No. 9,414,878, Aug. 16, 2019, Issued.
U.S. Appl. No. 14/667,421, filed Mar. 24, 2015, U.S. Pat. No. 9,700,364, Jul. 11, 2017, Issued.
U.S. Appl. No. 14/530,288, filed Oct. 31, 2014, U.S. Pat. No. 9,050,073, Jun. 9, 2015, issued.
U.S. Appl. No. 15/593,790, filed May 12, 2017, U.S. Pat. No. 10,251,693, Apr. 9, 2019, Issued.

JP 2016-526033—First Office Action dated Jan. 9, 2018, 7 pages.
JP 2016-526033—Request for Examination and Voluntary Amendment filed Sep. 26, 2017, 32 pages.
JP 2016-526033—Response to First Office Action dated Jan. 9, 2018, as filed Mar. 29, 2018, 24 pages.
JP 2016-526033—Response to Second Office Action dated May 8, 2018, 4 pages.
JP 2016-526033—Second Office Action dated May 8, 2018, 2 pages.
JP 2017-559683—1st Office Action dated Apr. 24, 2018, 5 pages.
JP 2018-140150—Request for Examination and Voluntary Amendment filed Aug. 24, 2018, 23 pages.
PCT/US2009/064395—International Preliminary Report on Patentability dated Jun. 3, 2011, 9 pages.
PCT/US2009/064395—Search Report and Written Opinion dated Feb. 3, 2010, 14 pages.
PCT/US2014/063518—International Preliminary Report on Patentability dated May 3, 2016, 9 pages.
PCT/US2014/063518—International Search Report and Written Opinion dated Feb. 9, 2015; 15 pages.
PCT/US2016/032125—International Preliminary Report on Patentability dated Nov. 30, 2017, 5 pages.
PCT/US2016/032125—International Search Report and Written Opinion dated Aug. 25, 2016, 5 pages.
PCT/US2017/032467—International Preliminary Report on Patentability dated Nov. 20, 2018.
PCT/US2017/032467—International Search Report and Written Opinion dated Aug. 21, 2017, 17 pages.
JS U.S. Appl. No. 13/766,567—Response to Restriction Requirement dated Nov. 19, 2013 filed Dec. 11, 2013, 6 pages.
U.S. Appl. No. 14/530,288—Notice of Allowance dated Mar. 31, 2015, 8 pages.
U.S. Appl. No. 14/530,288—Office Action dated Jan. 14, 2015, 12 pages.
U.S. Appl. No. 14/530,288—Response to Office Action dated Jan. 14, 2015 filed Mar. 18, 2015, 20 pages.
U.S. Appl. No. 14/667,421—Final Office Action dated Nov. 10, 2016, 12 pages.
U.S. Appl. No. 14/667,421—Final Office Action dated Feb. 3, 2016, 10 pages.
U.S. Appl. No. 14/667,421—Notice of Allowance dated Mar. 6, 2017, 8 pages.
U.S. Appl. No. 14/667,421—Office Action dated Jun. 13, 2016, 10 pages.
U.S. Appl. No. 14/667,421—Office Action dated May 14, 2015, 9 pages.
U.S. Appl. No. 14/667,421—Response to Final Office Action dated Nov. 10, 2016 filed Feb. 10, 2017, 7 pages.
JS U.S. Appl. No. 14/667,421—Response to Final Office Action dated Feb. 3, 2016 Office filed May 3, 2016, 6 pages.
U.S. Appl. No. 14/667,421—Response to Office Action dated Jun. 13, 2016 filed Aug. 9, 2016, 6 pages.
U.S. Appl. No. 14/667,421—Response to Office Action dated May 14, 2015 filed Sep. 24, 2015, 6 pages.
U.S. Appl. No. 14/714,101—Notice of Allowance dated Apr. 18, 2016, 9 pages.
U.S. Appl. No. 14/714,101—Office Action dated Nov. 27, 2015, 12 pages.
U.S. Appl. No. 14/714,101—Response to Office Action dated Nov. 27, 2015 filed Feb. 23, 2016, 8 pages.
U.S. Appl. No. 15/593,790—Office Action dated Dec. 14, 2017, 19 pages.
U.S. Appl. No. 15/593,790—Office Action dated May 29, 2018, 19 pages.
U.S. Appl. No. 14/876,035—Response to Office Action dated May 29, 2018 filed Aug. 21, 2019, 7 pages.
U.S. Appl. No. 14/876,035—Notice of Allowance Apr. 9, 2019, 8 pages.
CN 200980146533.8—1st Office Action dated Dec. 5, 2012, 9 pages with translatation included.
CN 200980146533.8—2nd Office Action dated Aug. 19, 2013, 14 pages with translation included.

(56) References Cited

OTHER PUBLICATIONS

CN 200980146533.8—Notice of Allowance dated Feb. 25, 2014, 2 pages.
CN 200980146533.8—Response to 1st Office Action dated Dec. 5, 2012 filed Apr. 9, 2013, 14 pages with translation included.
CN 200980146533.8—Response to 2nd Office Action dated Aug. 19, 2013 filed Oct. 21, 2013, 11 pages with translation included.
CN 201480058955.0—First Office Action dated Feb. 28, 2017, 9 pages.
CN 201480058955.0—Notice of Allowance dated Sep. 8, 2017, 4 pages.
CN 201480058955.0—Response to First Office Action dated Feb. 28, 2017, filed Jul. 14, 2017, 15 pages.
EP 09828054.8—1st Office Action dated Jan. 23, 2013, 4 pages.
EP 09828054.8—Extended EP Search Report dated Apr. 19, 2012, 8 pgs.
EP 09828054.8—Notice of Allowance dated Jul. 15, 2013, 75 pages.
EP 09828054.8—Response to Extended EP Search Report dated Apr. 19, 2012 filed Nov. 16, 2012, 30 pages.
EP 09828054.8—Response to first Office Action dated Jan. 23, 2013 filed May 16, 2013, 11 pages.
EP 14858416.2—Extended European Search Report dated Jun. 22, 2017, 16 pages.
EP 14858416.2—First Office Action dated Jun. 27, 2018, 7 pages.
EP 14858416.2—Response to Extended European Search Report dated Jun. 22, 2017 filed Jan. 19, 2018, 24 pages.
EP 14858416.2—Response to First Office Action dated Jun. 27, 2018, 16 pages.
JP 2011537520—1st Office Action dated Dec. 20, 2012, 8 pages.
JP 2011537520—2nd Office Action dated Oct. 10, 2013, 5 pages with translation included.
JP 2011537520—Notice of Allowance dated Jun. 5, 2014, 3 pages.
JP 2011537520—Response to 1st Office Action dated Dec. 20, 2012 filed Apr. 22, 2013, 16 pages with translation included.
JP 2011537520—Response to 2nd Office Action dated Oct. 10, 2013 filed Apr. 10, 2014, 13 pages.
JP 2014080934—1st Office Action dated Jan. 6, 2015, 6 pages with translation included.
JP 2015076854—1st Office Action dated Jan. 9, 2016, 5 pages.
JP 2015076854—Notice of Allowance dated Sep. 27, 2016, 3 pages.
JP 2015076854—Response to first Office Action dated Jan. 9, 2016 filed Apr. 25, 2016, 7 pages.
JP 2016-230681—Notice of Allowance dated Sep. 26, 2017, 3 pages.
JP 2016-230681—Request for Examination and voluntary amendment filed Dec. 28, 2016, 17 pages.
JP 2016-526033—Notice of Allowance dated Jun. 26, 2018, 3 pages.
CN 201780039970.4—Voluntary Amendments filed May 6, 2019, 22 pages.
CN 201780039970.4—First Office Action dated Dec. 3, 2020, 13 pages.
EP 17799918-2—Voluntary Amendments filed Jul. 23, 2019, 16 pages.
EP 17799918-2—Extended European Search Report dated Jan. 23, 2020, 10 pages.
EP 17799918-2—Response to Extended European Search Report dated Aug. 14, 2020, 18 pages.
AU 2017267476—Voluntary Amendments filed on Jan. 15, 2019, 19 pages.
AU 2017267476—Request for Exam and Amendment filed on Oct. 29, 2020, 17 pages.
KR 10-2018-7036573—Voluntary Amendments filed Dec. 17, 2018, 122 pages.
CN 201780039970.4—First Office Action dated Dec. 3, 2020, 11 pages.
CN 201780039970.4—Response to First Office Action dated Dec. 3, 2020, filed Apr. 15, 2021.
JP 2018-561003—First Office Action dated May 25, 2021, 17 pages.
U.S. Appl. No. 16/171,233—Non Final Office Action dated Dec. 11, 2020, 13 pages.
U.S. Appl. No. 16/171,233—Final Office Action dated Jun. 25, 2021, 13 pages.
U.S. Appl. No. 15/593,790—Notice of Allowance dated Nov. 23, 2018, 7 pages.
CN 201780039970.4 Certificate of Grant, dated Aug. 11, 2021, 2 pages.
AU 2017267476—First Office Action dated Jun. 3, 2021, 4 pages.
KR 10-2018-7036573—First Office Action dated May 25, 2021, 17 pages.
KR 10-2018-7036573—Response to First Office Action dated May 25, 2021, filed Jul. 20, 2021, 125 pages.
EP 14858416.2—Second Office Action dated May 18, 2020, 11 pages.
EP 14858416.2—Response to Second Office Action dated May 4, 2020, filed Sep. 10, 2020, 10 pages.
EP 14858416.2—Communication Under Rule 71(3) EPC dated Oct. 26, 2020, 38 pages.
U.S. Appl. No. 15/211,365—Notice of Allowance dated Jun. 13, 2018, 43 pages.
U.S. Appl. No. 16/171,233—Advisory Action dated Sep. 14, 2021, 4 pages.
CN 201711084674.4—First Office Action dated Sep. 26, 2019, 19 pages.
CN 201711084674.4—Second Office Action dated Mar. 16, 2020, 16 pages.
JP 2018-140150—First Office Action dated Sep. 24, 2019, 10 pages.
JP 2018-140150—Second Office Action dated Jun. 2, 2020, 6 pages.
CN 201680024610.2—First Office Action dated Aug. 1, 2018, 8 pages.
CN 201680024610.2—Response to First Office Action dated Aug. 1, 8 pages.
CN 201680024610.2—Notice of Allowance dated Jan. 30, 2019, 2 pages.
JP 2017-559683—First Office Action dated Apr. 24, 2018, 4 pages.
JP 2017-559683—Response to First Office Action dated Apr. 24, 2018, filed Jul. 20, 2018, 8 pages.
JP 2017-559683—Notice of Allowance dated Jul. 31, 2018, 3 pages.
EP 16796979.9—First Office Action dated Jan. 25, 2019, 9 pages.
EP 16796979.9—Response to First Office Action dated Jan. 25, 2019, as filed on May 29, 2019, 16 pages.
AU 2017267476—Notice of Acceptance dated Oct. 14, 2021, 3 pages.
U.S. Appl. No. 16/171,233—Notice of Allowance dated Oct. 22, 2021, 8 pages.
CN 201711084674.4 Notice of Allowance, dated Aug. 17, 2020, 3 pages.
JP 2018-140150—Notice of Allowance, dated Dec. 1, 2020, 5 pages.
EP 16796979.9 Decision to Grant, dated Jan. 30, 2020, 2 pages.
JP 2018-161000 First Office Action, dated Apr. 21, 2020, 4 pages.
JP 2018-161000 Notice of Allowance, dated Jun. 30, 2020, 5 pages.
CN 201910265462.9 Notice of Grant, dated Jun. 3, 2021, 4 pages.
JP 2018-561003 Notice of Allowance, dated Jan. 4, 2022, 5 pages.
KR 10-2018-7036573 Decision to Grant, dated Nov. 22, 2021, 3 pages.
U.S. Appl. No. 15/211,365 Supplemental Notice of Allowance, dated Jun. 25, 2018, 10 pages.

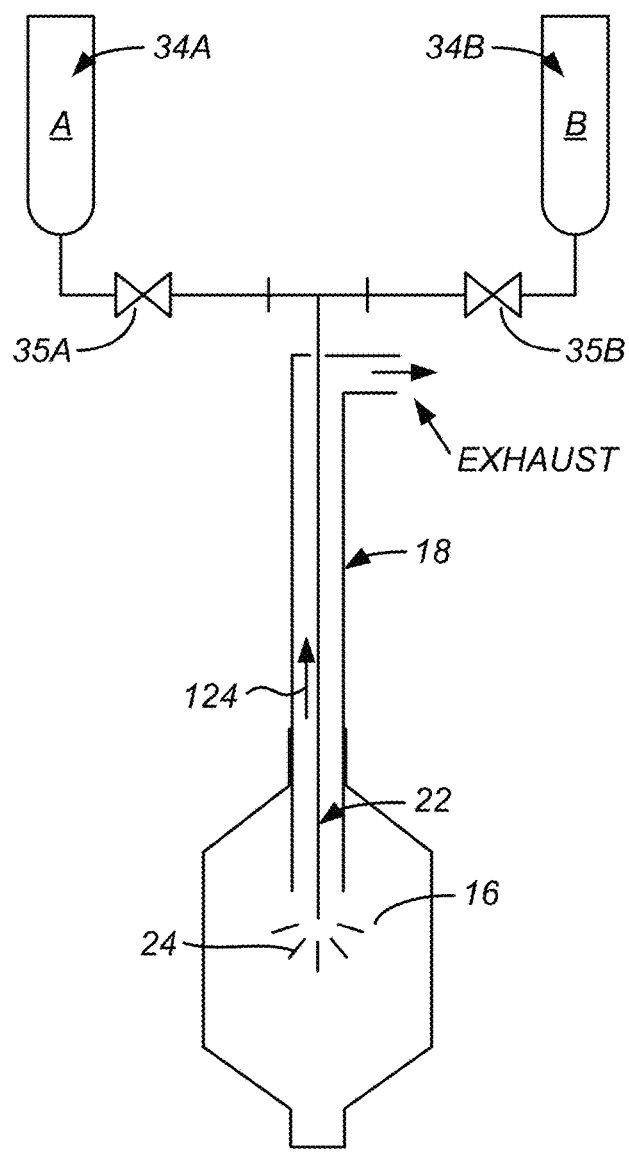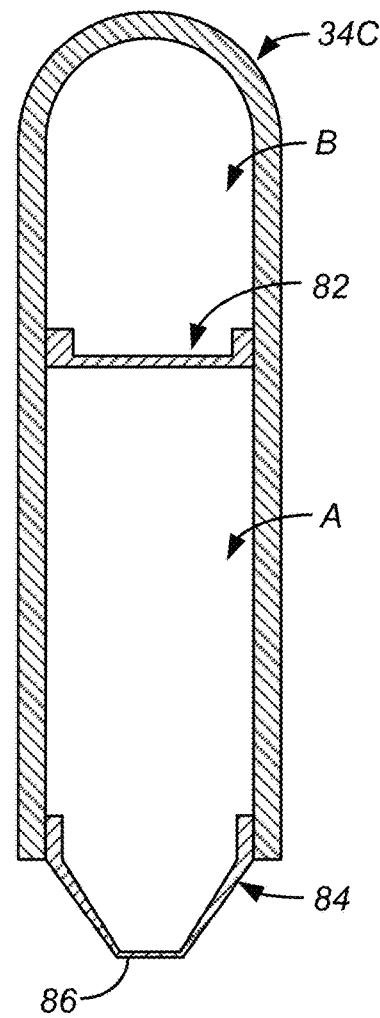
FIG. 12
FIG. 13

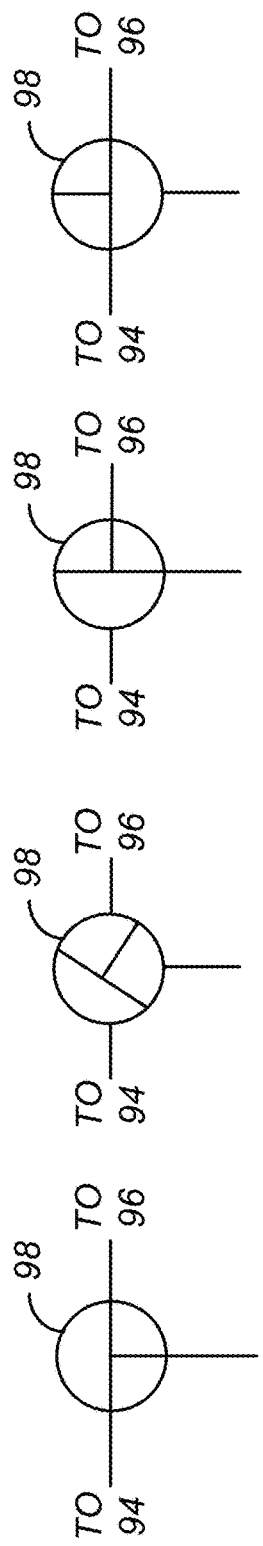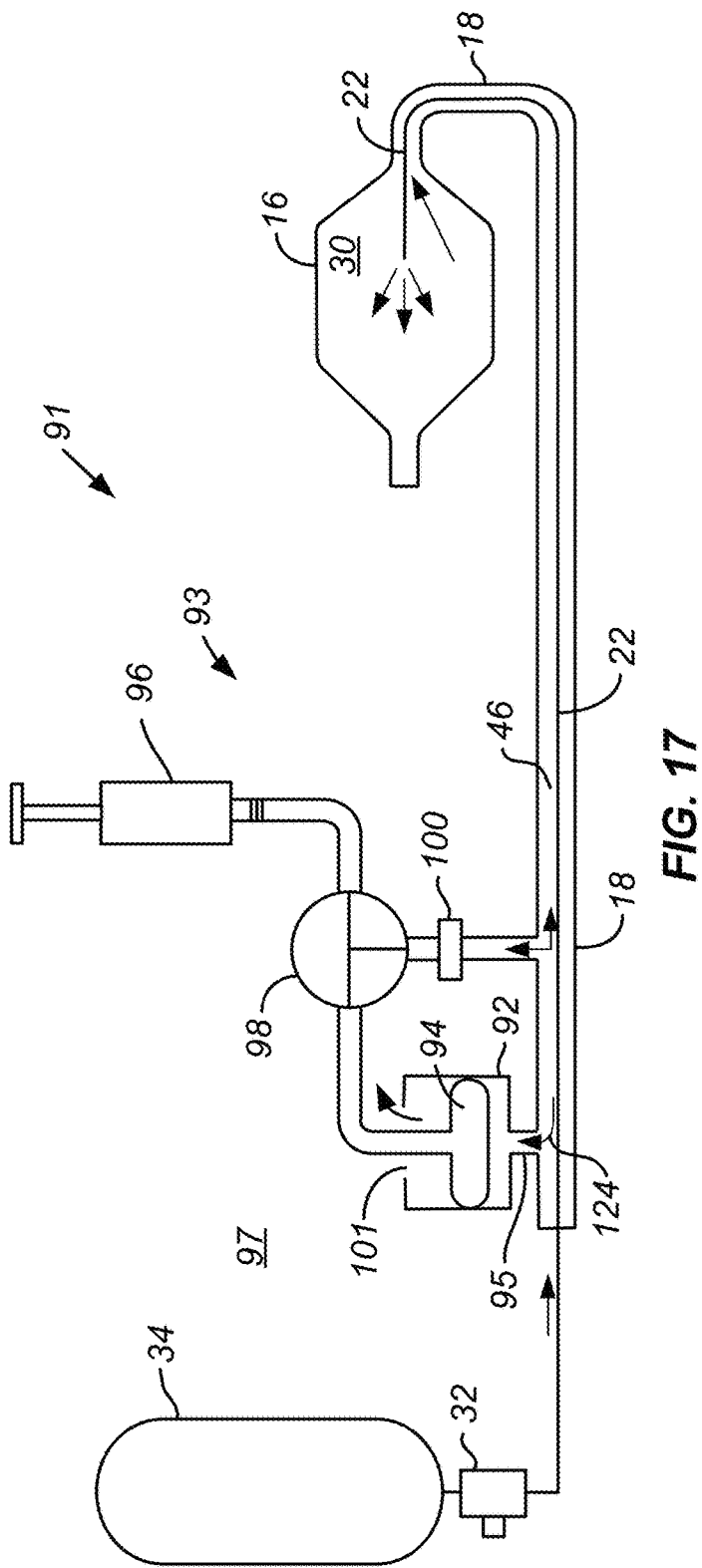

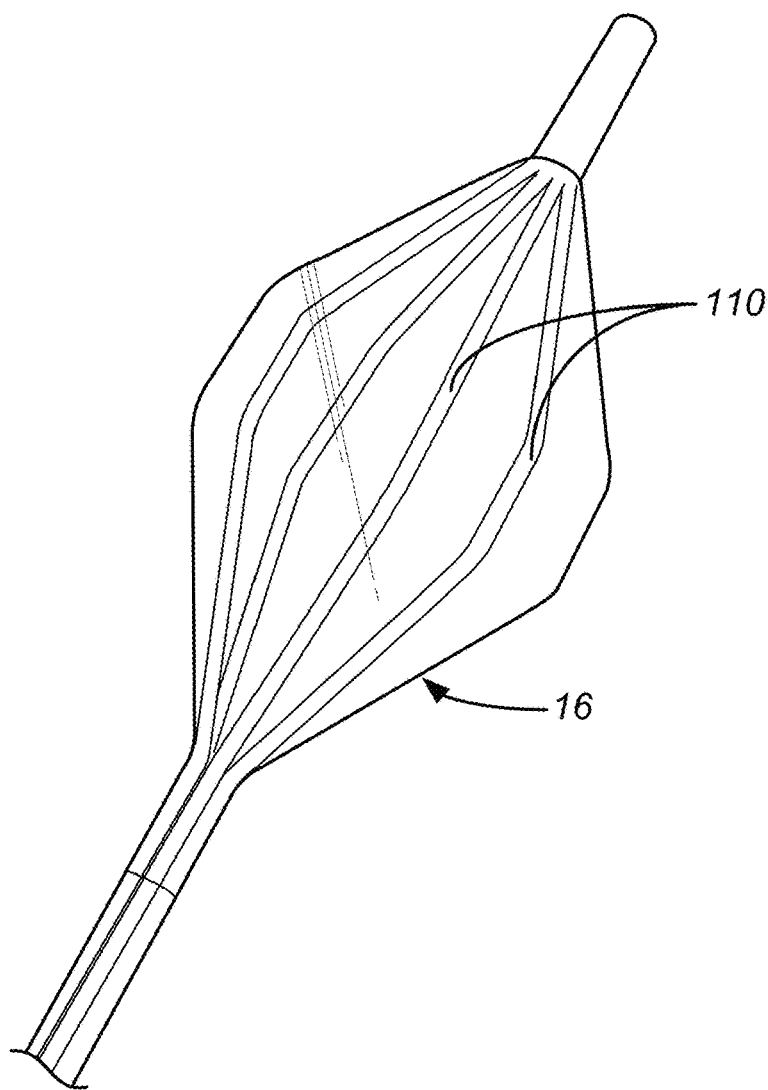
FIG. 22
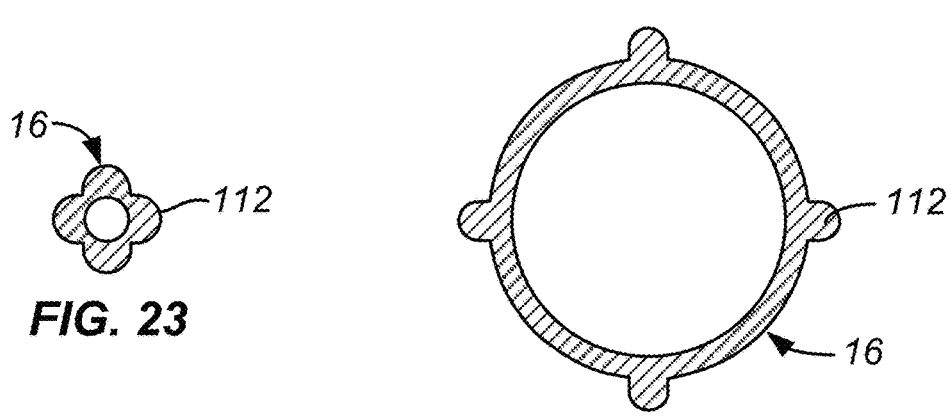
FIG. 23
FIG. 24

CRYOGENIC ABLATION SYSTEM AND METHOD

CROSS-REFERENCE TO OTHER APPLICATIONS

This application is a continuation of U.S. patent application Ser. No. 14/876,035, filed 6 Oct. 2015, now U.S. Pat. No. 10,383,676, issued Aug. 20, 2019; which application is a continuation of U.S. patent application Ser. No. 13/766,567, filed 13 Feb. 2013, now U.S. Pat. No. 9,168,081, issued 27 Oct. 2015; which application is a divisional of U.S. patent application Ser. No. 12/611,057, filed 2 Nov. 2009, now U.S. Pat. No. 8,382,746, issued 26 Feb. 2013; which application claims the benefit of U.S. provisional patent application No. 61/116,991, filed 21 Nov. 2008.

FEDERALLY SPONSORED RESEARCH OR DEVELOPMENT

None.

BACKGROUND OF THE INVENTION

Throughout the human body there are lumens, such as the esophagus and colon, which may have components which may become metaplastic or neoplastic. Often, it is desirable to remove or destroy these unwanted tissues. One of these cases where tissue removal and/or ablation are desirable is Barrett's Esophagus, which is a pre-cancerous condition of the esophagus typically often associated with gastric reflux disease (GERD). Although GERD can be medically controlled, Barrett's Esophagus does not spontaneous resolve once the GERD has abated. However, it has been shown that if Barrett's Esophagus is ablated, the normal esophagus lining can be restored and therefore lower the risk of developing esophageal cancer.

A variety of techniques have been evaluated for ablation of this condition. These techniques include photodynamic therapy, endoscopic resection of the lining of the esophagus, and ablation using a variety of energy sources such as argon plasma coagulation (APC), radio-frequency (RF) and cryogenic via a direct spray of liquid nitrogen.

BRIEF SUMMARY OF THE INVENTION

An example of a medical device for treating esophageal target tissue comprises a catheter, a balloon and a refrigerant delivery device. The catheter includes proximal and distal portions and a refrigerant delivery lumen. The catheter also defines a longitudinally extending catheter axis. The balloon is mounted to the distal portion. The balloon has an inner surface defining a balloon interior. The refrigerant delivery device is coupled to the distal portion. The refrigerant delivery device comprises a chamber with the refrigerant delivery lumen opening into the chamber, a refrigerant delivery opening fluidly coupled to the balloon interior, and a distribution passageway fluidly coupling in the chamber and the refrigerant delivery opening. A refrigerant is deliverable through the refrigerant delivery lumen, into the chamber, through the distribution passageway, through the refrigerant delivery opening and into the balloon interior so to place the balloon into an expanded, cooled state so that the balloon can press against and cool esophageal target tissue.

In some examples the balloon surrounds at least the portion of the refrigerant delivery device that comprises the refrigerant delivery opening. In some examples the medical device further comprises means for sensing a leak in the balloon. In some examples the distribution passageway comprises an annular passageway having a length generally parallel to and surrounding the catheter axis.

In some examples the refrigerant delivery device comprises a flow deflector tube, through which the refrigerant delivery opening is formed, and an axially-positionable flow director sleeve at least partially surrounding the flow deflector tube. At least one of the (1) refrigerant delivery opening, and (2) the flow director sleeve, has an edge extending at least partially around the catheter axis and along a path having changing rotary and axial positions. The flow deflector sleeve can be positioned to cover all or part of the refrigerant delivery opening to affect the delivery of refrigerant into the balloon interior.

Another example of a medical device for treating esophageal target tissue comprises a catheter, a balloon and a refrigerant delivery device. The catheter comprises a main shaft having an open interior, distal portion, an exhaust lumen, and a refrigerant delivery lumen. The distal portion has a smaller outside diameter than the main shaft. The balloon comprises a larger diameter main portion and a smaller diameter stem portion at a proximal end thereof. The smaller diameter stem portion is mounted to the distal portion of the catheter. The balloon comprises an inner surface defining a balloon interior. The refrigerant delivery device is coupled to the distal portion. The refrigerant delivery device comprises a chamber, with the refrigerant delivery lumen opening into the chamber, and a refrigerant delivery opening fluidly coupled to the chamber and opening into the balloon interior. A refrigerant is deliverable through the refrigerant delivery lumen, into the chamber, through the refrigerant delivery opening and into the balloon interior so to place the balloon into an expanded, cooled state so that the balloon can press against and cool esophageal target tissue.

An example of a method for making a medical device for cryogenically treating esophageal target tissue within a target tissue treatment temperature range includes the following. A target tissue treatment temperature range is determined for cryogenically ablating the target tissue. A balloon material is selected, the balloon material having a glass transition temperature above the target tissue treatment temperature range, and having elastic properties above the glass transition temperature, and being stretch-resistant below the glass transition temperature. A balloon made of the selected balloon material is mounted to a distal portion of a catheter assembly. The balloon comprises an inner surface defining balloon interior. The catheter assembly comprises a catheter comprising a refrigerant delivery lumen fluidly coupled to the balloon interior. A refrigerant can be delivered through the refrigerant delivery lumen and into the balloon interior so to place the balloon into an expanded, cooled state with the temperature of the balloon lower than the glass transition temperature thereby substantially preventing any further expansion of the balloon while the balloon cools the esophageal target tissue.

An example of a controlled balloon expansion assembly, for use with a balloon placeable within an open region of a body, the balloon having an interior and being placeable in inflated and deflated states, includes an exhaust passageway device and a relief valve assembly. The exhaust passageway device defines an exhaust passageway coupleable to the balloon interior. The relief valve assembly comprises a relief valve, a pressurization device and valving. The relief valve comprises a chamber having an inlet fluidly coupled to the exhaust passageway, an outlet fluidly coupled to an exhaust gas dumping region, and a pressure sensitive sealing element between the inlet and the outlet. The sealing element is configured to provide a seal between the inlet and the outlet according to a level of pressure applied to the sealing element. The valving selectively fluidly couples the pressurization device to and fluidly isolates the pressurization device from the sealing element and the exhaust passageway. In some examples the valving comprises a control valve placeable in the following states. A first state fluidly couples the pressurization device, the pressure sensitive sealing element and the exhaust passageway to one another. A second state fluidly isolates the pressurization device, the pressure sensitive sealing element and the exhaust passageway from one another. A third state fluidly couples the pressurization device to the exhaust passageway. A fourth state fluidly couples the pressurization device to the pressure sensitive sealing element.

Other features, aspects and advantages of the present invention can be seen on review the figures, the detailed description, and the claims which follow.

BRIEF DESCRIPTION OF THE DRAWINGS

FIG. 12 illustrates apparatus for selectively coupling two different refrigerant cylinders to the refrigerant delivery tube;

FIG. 13 illustrates a refrigerant cylinder with two different refrigerants contained within the cylinder and separated by a divider/rupture disk;

FIG. 17 shows apparatus to help prevent the balloon from exerting excessive force against the vessel wall;

FIGS. 17A, 17B, 17C and 17D illustrate the control valve of FIG. 17 in four different positions;

FIG. 22 is a view of a balloon reinforced through the use of a high-strength adhesive directly to the balloon;

FIGS. 23 and 24 are simplified cross-sectional views of a reinforced balloon having a variable thickness wall shown in contracted and expanded states;

DETAILED DESCRIPTION OF THE INVENTION

The following description of the invention will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows.

All of the techniques listed above for ablation of Barrett's Esophagus suffer from 'usability' drawbacks. Photodynamic therapy renders the patient susceptible to sunlight for several months following treatment and has a high procedural complication rate. Mechanical resection is training intensive and may not achieve 100% removal of the condition. Ablation techniques such as APC only treat a small area at a time and controlling the depth of ablation is difficult. Current RF ablation techniques require precise sizing of the treatment catheter and require another console for the physician to operate. The direct spray of liquid nitrogen can be training intensive and is very operator dependent; this system also requires an additional console and a constant supply of liquid nitrogen.

The present invention addresses many of the limitations of the current technologies. The invention is particularly useful for treating Barrett's esophagus but may also be useful for treating other esophageal tissues, typically by cryogenic ablation of the atypical tissue.

Figure 1:
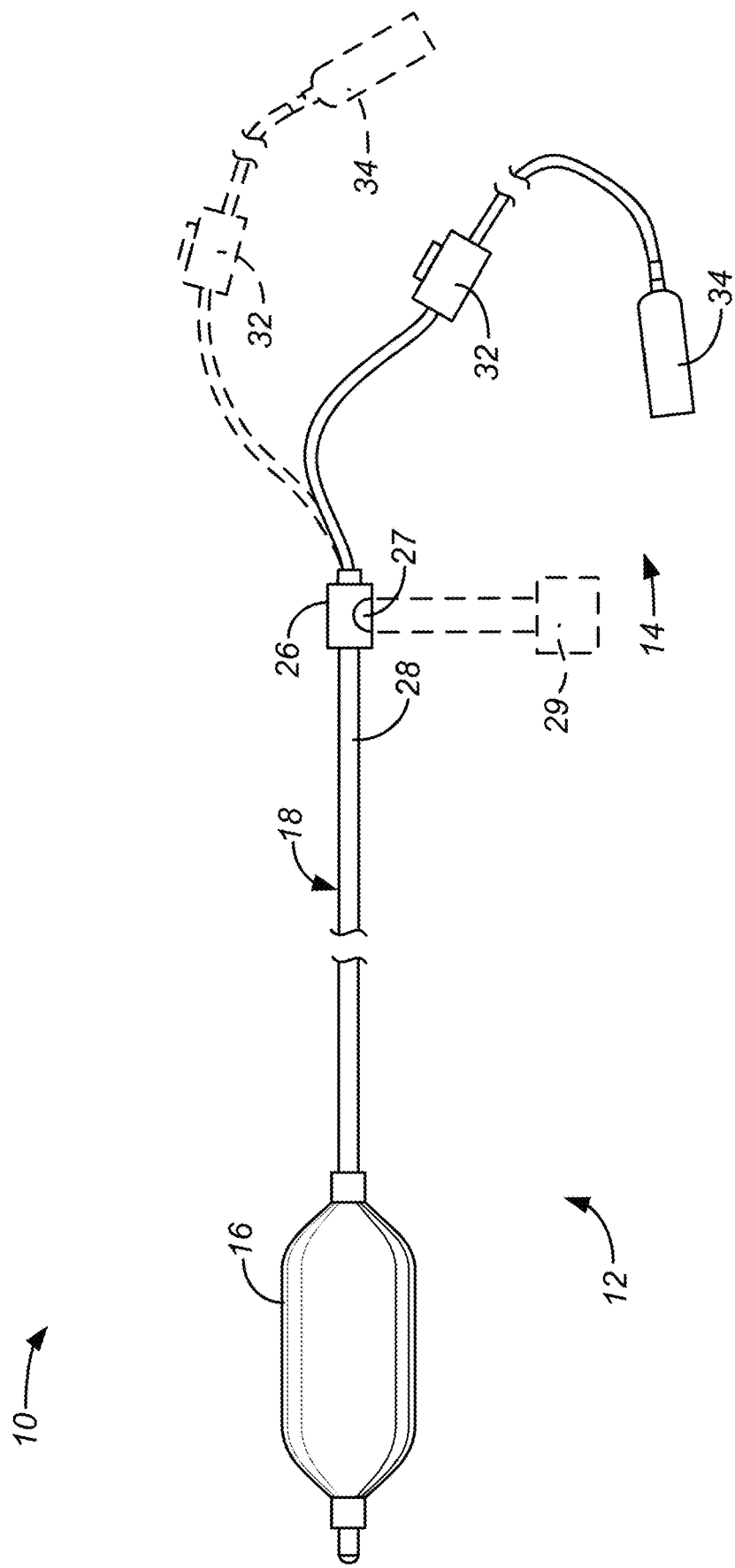
FIG. 1 is a simplified overall view of one example of a medical device made according to the invention with elements of other examples shown in dashed lines.
Figure 2:
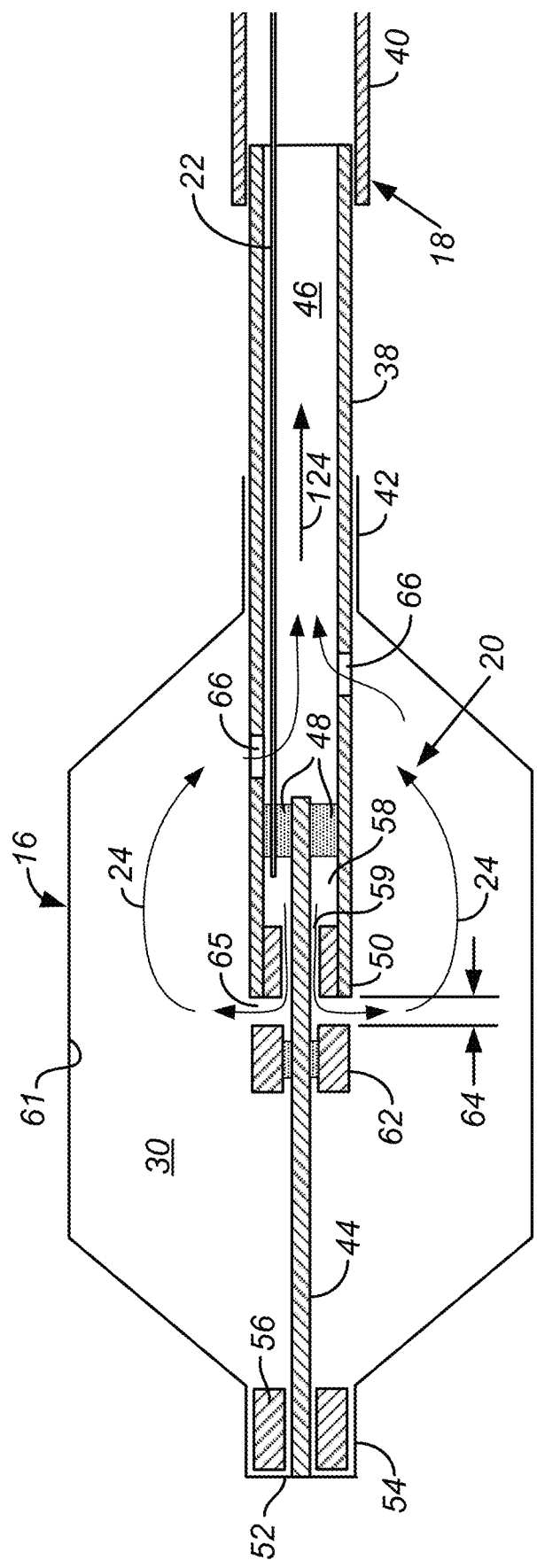
FIG. 2 is an enlarged, simplified cross-sectional view of the distal portion of a first example of the medical device of FIG. 1.

According to some embodiments of the invention, see FIGS. 1 and 2, the medical device 10 comprises a catheter assembly 12 and a refrigerant supply 14. The catheter assembly 12 comprises a balloon 16, preferably an elastomeric material such as polyurethane or silicone, mounted to a placement catheter or shaft 18. In one embodiment the balloon 16 will be capable of producing an inflated diameter of between 15-45 mm. In another embodiment, multiple balloon sizes may be required to cover the desired range of esophagus sizes; in this embodiment, it is desirable to have individual balloon diameters that are variable by at least 2 mm. For example, 6 different sizes could be developed to cover the complete range of 15-45 mm in which case each size covers a 5 mm range. The balloon length may be 10-100 mm. The shaft 18 may comprise a plastic such as polyurethane such that the balloon may be appropriately bonded to the shaft; other appropriate, biocompatible materials such as PEBAX and polyethylene may also be used. The shaft 18 will typically be less than 8-Fr if it is to be compatible with a conventional diagnostic endoscope, which typically has an accessory channel size of 2.8 mm. However, larger shaft sizes up to, for example, 11-Fr may be used for catheters designed for conventional therapeutic endoscopes. Shaft 18 may include a refrigerant delivery lumen, not separately illustrated, formed within a separate refrigerant delivery tube 22 which may be used for delivery of the refrigerant. Delivery tube 22 is shown running through, and may be concentric with, the shaft 18 and may have an inner diameter of, for example, 0.004-0.025" (0.10-0.71 mm). In some embodiments all or part of delivery tube 22 could also pass along the exterior of shaft 18. This delivery tube 22 may comprise a high-strength plastic material such as polyimide. Alternatively, delivery tube 22 may comprise a metal hypotube. Typical metals for hypotube include stainless steel and nitinol. In other embodiments, the placement shaft 18 itself will define at least a portion of the refrigerant delivery lumen.

Medical device 10 also includes a refrigerant delivery device 20 at the distal end 38 of shaft 18. A fluid saturated liquid/gas refrigerant 24, indicated by arrows 24 in FIG. 2, such as nitrous oxide or a hydrofluorocarbon, is provided from the refrigerant supply 14 through a manifold 26 at the proximal end 28 of the shaft 18, through the refrigerant delivery lumen defined within the delivery tube 22, through refrigerant delivery device 20, and into the interior 30 of the balloon 16. As shown in FIG. 1, one example of a refrigerant supply 14 of medical device 10 comprises a flow control device 32 which may be hand-held, coupled to a disposable cylinder 34 of refrigerant. The size of the cylinder 34 may be, for example, between 10 to 50 cubic centimeters in volume. The refrigerant supply 14 may be integral to the catheter assembly 12 or stand-alone. The refrigerant 24 will typically be continuously injected, at room temperature or warmer, through the lumen within the delivery tube 22 and in some embodiments will exit into the interior 30 of the balloon 16. The refrigerant will then undergo a phase change from liquid to gas, simultaneously expanding the balloon and rapidly drawing energy from the surrounding esophageal tissue and causing the tissue to be cooled. The gas may then exhaust though shaft 18 and exit out of the manifold 26 though an exit port 27. In some other embodiments, the refrigerant supply may require external heating to maintain the desired delivery pressure. The balloon 16 will then expand until contact with the tissue of the esophagus 36, shown in FIG. 9, has been made.

The placement of the balloon 16 at the target site and expansion of the balloon is preferably monitored by conventional techniques, such as direct endoscopic visualization. Other endoscopic spectroscopy techniques such as Fluorescence, Raman, or Light Scattering may be useful for identification of atypical esophageal tissue. In order to lower the risk of injury to the esophagus, the balloon pressure should be minimized such that the effective pressure applied to the esophagus is less than 10-psig. Balloon pressure is primarily dependent on the refrigerant flow rate and can be controlled by manipulating the sizes of the interior 46 of shaft 18 and/or the lumen of delivery tube 22. Pressure can also be controlled though a back-pressure regulator 29, shown in dashed lines in FIG. 1, attached to port 27. Techniques for controlling expansion of balloon 16 are described below.

Cooling of the esophagus, in particular the atypical esophageal tissue, is typically achieved by evaporation of liquid refrigerant in the balloon 16 which will draw heat away from the esophageal tissue at the target site. In order to ablate or otherwise alter the atypical tissue, it is desirable to cool this tissue until it has frozen. Typically, intracellular ice formation is required for substantial necrosis of the atypical tissue. The target temperature to achieve sufficient intracellular ice formation in the atypical esophageal tissue may be between −25 and −100° C. As undesirable side effects of the cryoablation treatment such as esophageal perforation or stricture may occur if necrosis occurs deeper than the mucosa, the depth of ablation may be controlled by regulating the time that the cooling is applied to the esophagus. Based on typical mucosal thickness of 0.5-2 mm, the required time for ablation may be less than 60 seconds.

FIG. 2 is a cross-sectional view of a distal portion of a first example of catheter assembly 12 illustrating refrigerant delivery device 20. The distal end 38 of shaft 18 has a smaller diameter than the main portion 40 of shaft 18. Thus, when the proximal end 42 of balloon 16 is secured to the outer surface of distal end 38 and is in its collapsed state, the overall diameter of balloon 16 surrounding distal end 38 of shaft 18 can be reduced compared with mounting the balloon to the larger diameter main portion 40.

Refrigerant delivery device 20 includes a support wire 44 having its proximal end secured within the interior 46 of shaft 18, typically with an adhesive or a potting compound 48. Support wire 44 passes from the tip 50 of shaft 18 and through the interior 30 of balloon 16. The tip 52 of support wire 44 is adhesively or otherwise secured to the distal end 54 of balloon 16 through a sleeve 56.

Refrigerant tube 22 passes through potting compound 48 with the tip of tube 22 opening into a chamber 58 defined by distal shaft end 38, potting compound 48 at one end and a tubular guide sleeve 60 at the other end. The central opening through guide sleeve 60 is oversized relative to support wire 44 to permit the passage of refrigerant 24 from chamber 58, through a distribution passageway 59 between support wire 44 and guide sleeve 60, and into interior 30 of balloon 16.

In addition to ablation depth control, uniform surface ablation over the entire surface of the target site is also necessary. To achieve this, and assuming the entire outer surface of the expanded balloon 16 is used to contact the target site, the liquid refrigerant must be uniformly applied to the full inner surface 61 of balloon 16. One method of full radial distribution is shown in FIG. 2. A sleeve like flow deflector 62 is secured to support wire 44, typically by an adhesive, a distance 64 from tip 50. The gap between flow deflector 62 and tip 50 creates a nozzle or jet 65 type of fluid delivery opening through which refrigerant 24 flows toward the inner surface of balloon 16. Distance 64 is typically about 0.025 mm-0.51 mm (0.001 inch-0.020 inch). This causes a refrigerant 24 to be radially deflected over a 360° angle so that the entire circumferential surface of balloon 16 is cooled by refrigerant 24. Refrigerant 24 exits interior 30 of balloon 16 through exhaust holes or ports 66 formed in distal end 38 of shaft 18 and into interior 46 of shaft 18, which acts as an exhaust lumen. In this example refrigerant delivery device 20 generally includes potting compound 48, guide sleeve 60, flow deflector 62 and support wire 44.

Figure 3:
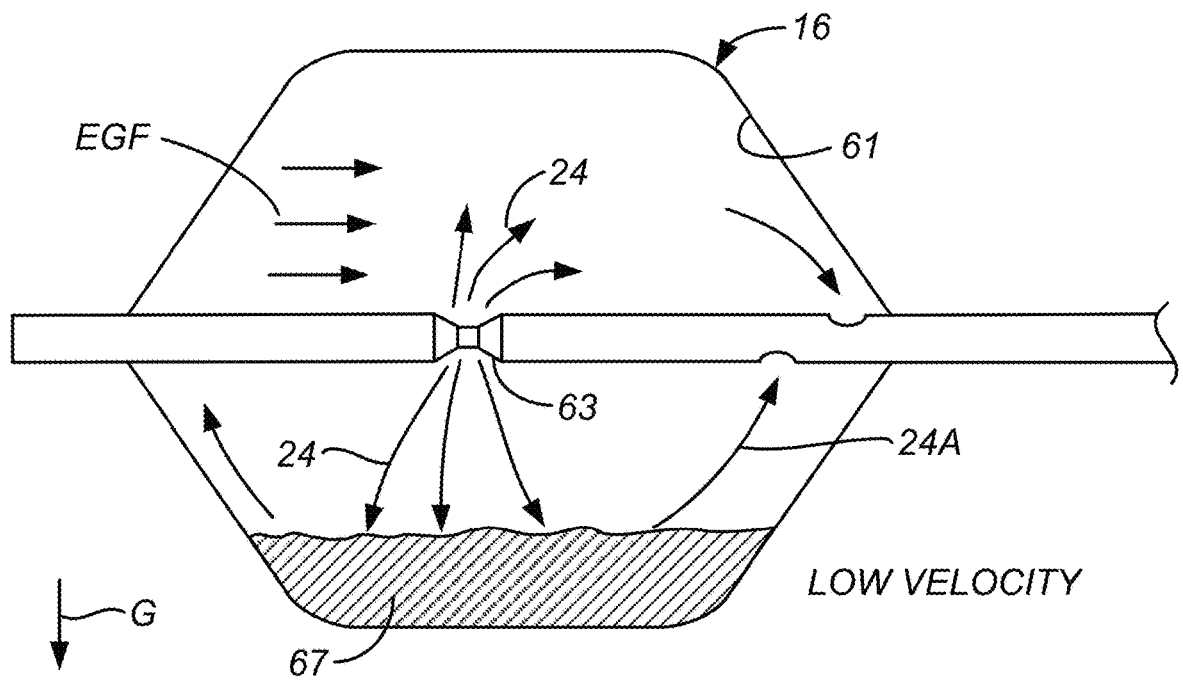
FIGS. 3 and 4 are simplified illustrations of the effects of high velocity and low velocity refrigerant flow into the balloon.
Figure 4:
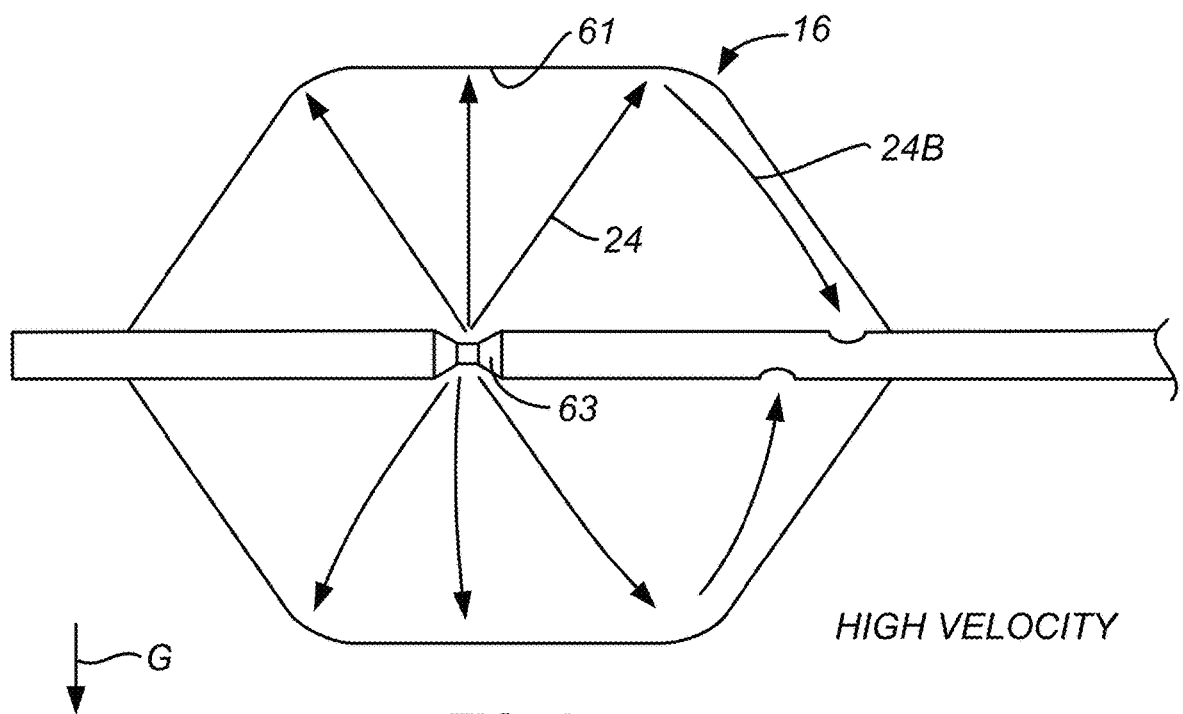

By increasing or reducing the cross-sectional area of the gap between support wire 44 and guide sleeve 60 and by adjusting distance 64, the velocity of the refrigerant can be increased or decreased as necessary to propel the refrigerant to reach the inner surface of the balloon. Typically, the gap between support wire 44 and sleeve 60 will be less than 0.127 mm (0.005 inches). This feature has significant importance as the diameter of a balloon 16 increases because refrigerant 24 has farther to travel to reach inner surface 61 of the balloon and is therefore increasingly affected by the two primary forces, gravity suggested by arrow G in FIGS. 3 and 4, and forces associated with the motion of the exhaust gas, suggested by arrows EGF. As shown in FIG. 3, when the velocity of the liquid refrigerant is too low, the refrigerant tends to form a pool 67 of refrigerant 24 on the bottom surface of the balloon 16. Furthermore, the exhaust gas refrigerant 24 tends to push a stream of liquid refrigerant 24A towards the exhaust ports 66. However, as shown in FIG. 4, when refrigerant 24 is expelled at a high velocity, the high velocity refrigerant 24 is able to overcome both gravity and the exhaust gas forces to fully coat the inside surface 61 of the balloon 16 with liquid refrigerant 24B. The shape of the deflecting surface 63 of deflector 62 can also be adjusted to modify the spray pattern.

Figure 5:
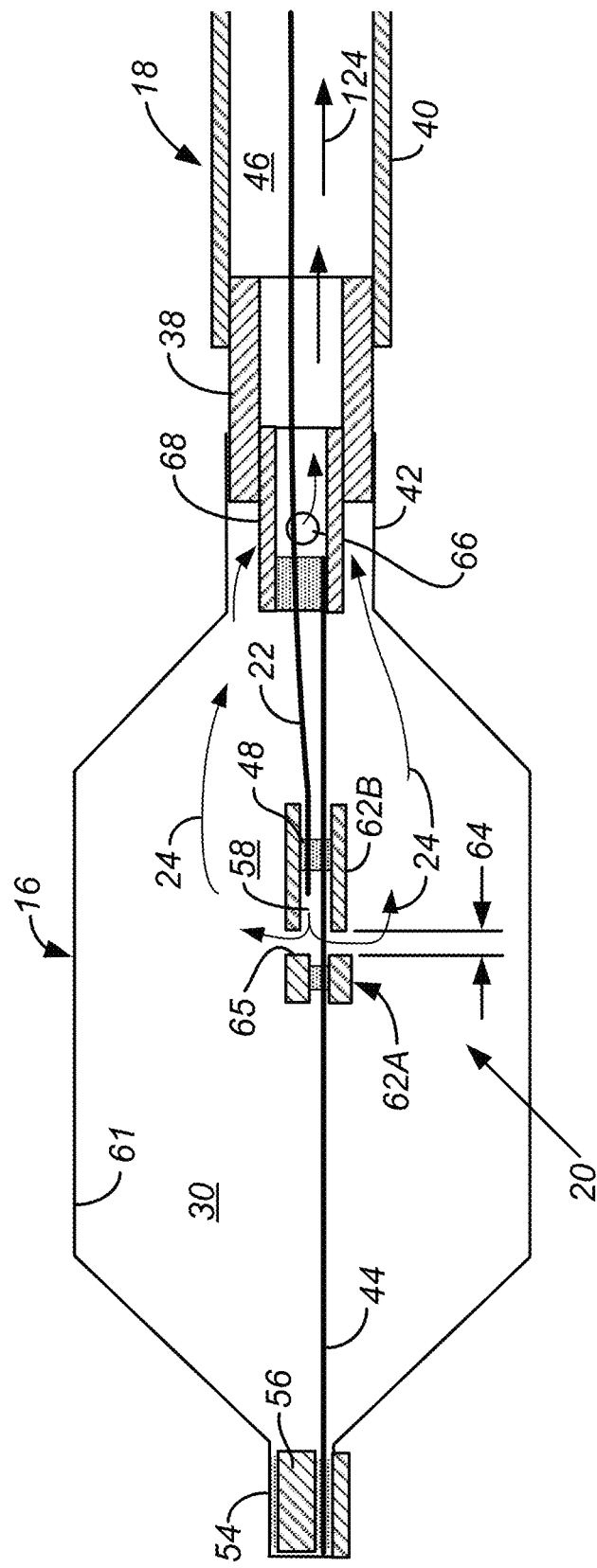
FIG. 5 is a view similar to that of a FIG. 2 of another example of the medical device FIG. 1.

FIG. 5 illustrates another embodiment in which the distal end 38 of shaft 18 is shorter than with the embodiment of FIG. 2. Refrigerant delivery device includes sleeve like flow deflector 62A and flow deflector sleeve 62B secured to support wire 44 and are separated to provide jets 65 therebetween. The distal end of refrigerant delivery tube 22 is secured within the interior of flow deflector sleeve 62B and opens into chamber 58, chamber 58 being defined within flow deflector sleeve 62B. In this embodiment refrigerant 24 passes directly from chamber 58 to jets 65. A reduced diameter exhaust sleeve 68 extends from distal end 38 and has one or more exhaust holes 66 formed therein through which exhaust gas 124 can flow. In this embodiment, the outside diameters of flow deflector 62A and flow deflector sleeve 62B can have a reduced diameter relative to the inside of the distal end 38 of shaft 18 to which proximal end 42 of balloon 16 is secured. This permits the profile of balloon 16 when in a collapsed or folded state to be reduced. In some examples exhaust sleeve 68 can be eliminated if support wire 44 is secured directly to distal end 38 while leaving distal end 38 sufficiently open at tip 50 to permit exhaust gas 124 to flow into the interior 46 of shaft 18.

Figure 6:
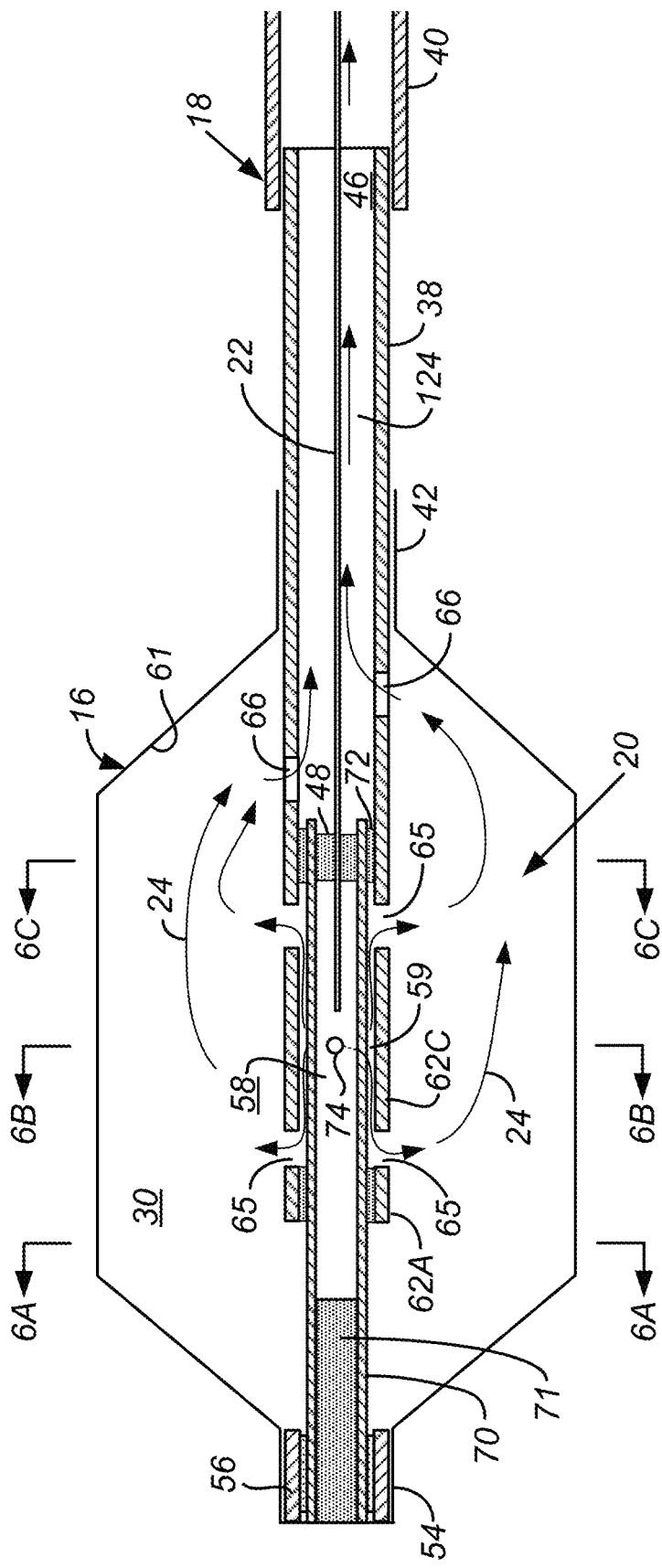
FIG. 6 is a view similar to that of FIG. 2 of further example of the medical device of FIG. 1.
Figure 6A:
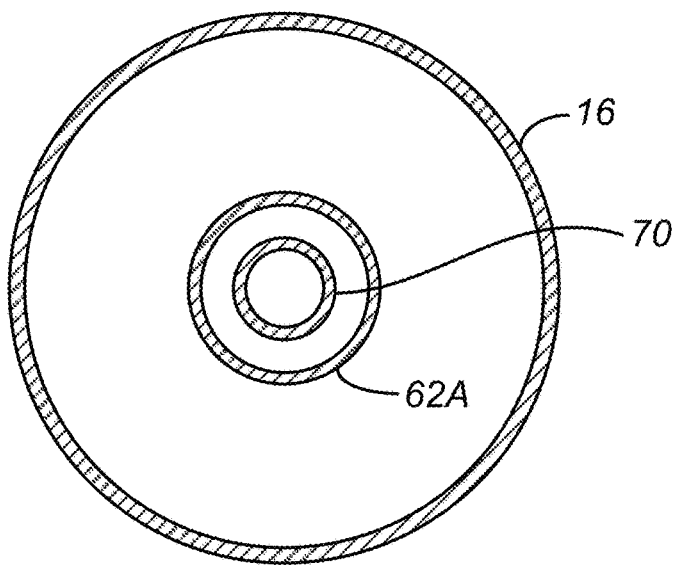
FIGS. 6A, 6B and 6C are cross-sectional views taken along corresponding lines of FIG. 6.
Figure 6B:
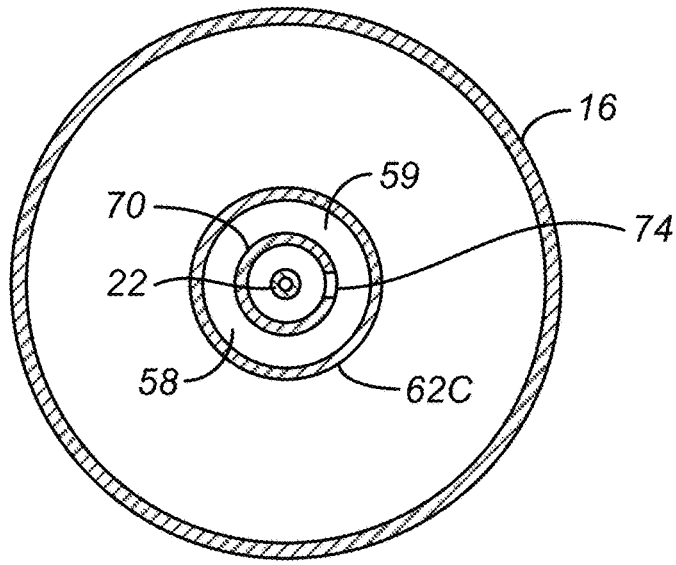
Figure 6C:
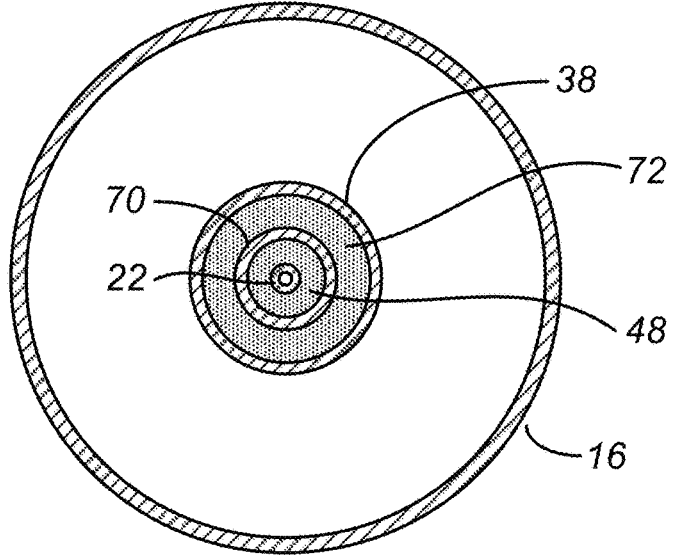
Figure 6D:
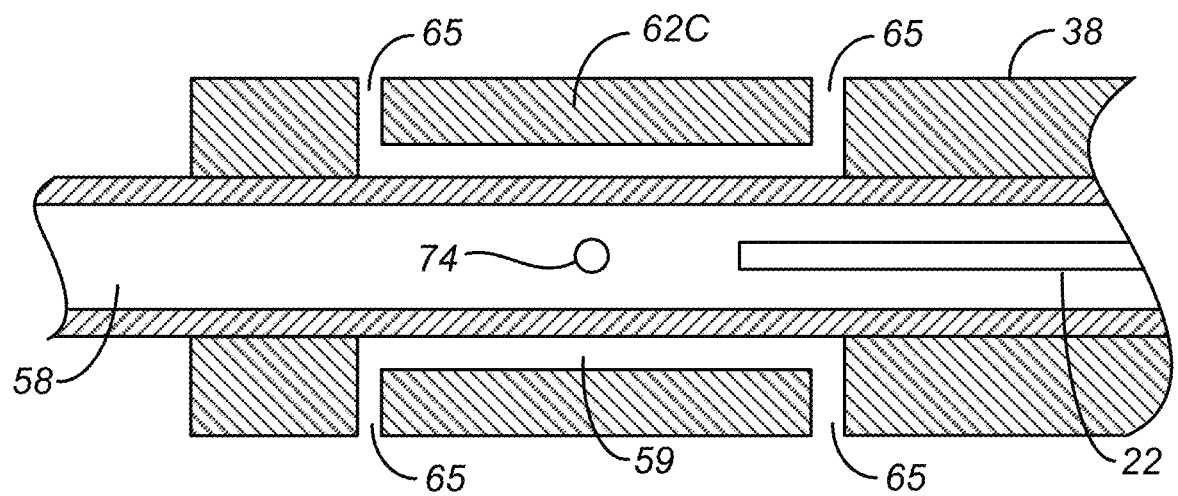
FIG. 6D is an enlarged view of a portion of FIG. 6.
Figure 7:
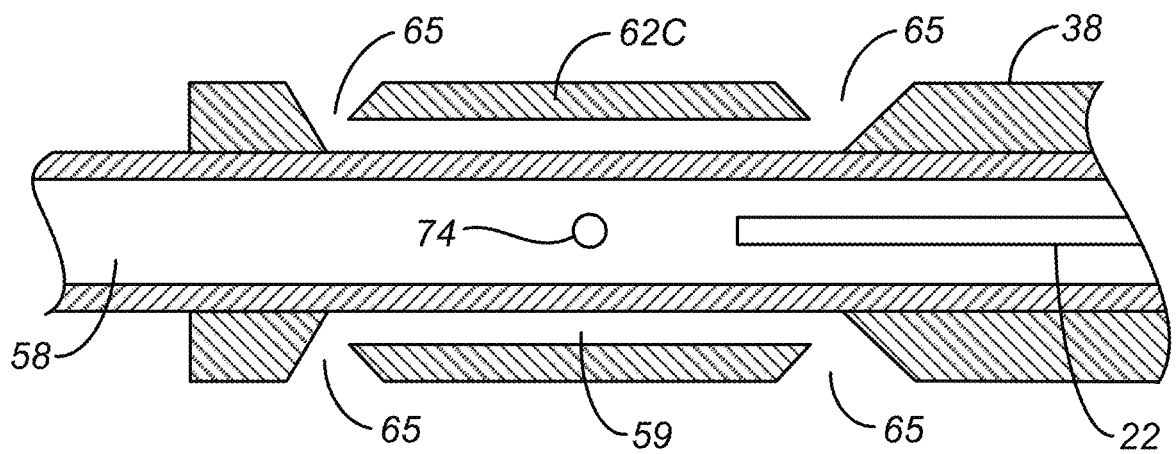
FIG. 7 is a view similar to that of FIG. 6D showing alternative shapes of refrigerant discharge jets.

FIGS. 6 and 7 illustrate a third embodiment in which multiple jets 65 are used to provide more uniform axial distribution of refrigerant 24. This is especially helpful for longer balloons. The embodiment of FIG. 6 differs from that of FIG. 2 in another manner. A delivery adapter tube 70 is fixed within distal end 38 of shaft 18, typically using an adhesive or potting compound 72. The distal end of tube 70 is filled with a potting compound 71 or other plug structure. Delivery adapter tube 70, potting compound 71, and potting compound 48 surrounding refrigerant delivery tube 22 define chamber 58. One or more holes 74 are formed in delivery adapter tube 70. Refrigerant 24 passes through holes 74 and into distribution passageway 59 defined between delivery adapter tube 70 and flow deflector sleeve 62C. Refrigerant 24 then passes through jets 65 into interior 30 of balloon 16. The use of distribution passageways 59 in the embodiments of FIGS. 2 and 6 between chamber 58 and jets 65 helps to ensure proper distribution, typically substantially even distribution, of refrigerant 24 to jets 65. Distribution passageways 59 thus act as simple manifolds for the proper distribution of refrigerant 24.

The embodiment of FIG. 6 uses flow deflector 62A and flow deflector sleeve 62C which are separate elements from distal end 38 of shaft 18. This enables jets 65 to be full, 360° delivery jets. While flow deflector sleeve 62C may be affixed to adapter tube 70 at, for example, three circumferentially spaced positions, in some embodiments it may be free-floating on the adapter tube 70 so that the pressure of refrigerant 24 causes flow deflector sleeve 62C to become centered on tube 70. Other examples may have flow deflector 62A and flow deflector sleeve 62C be extensions of the distal end 38 of shaft 18.

In another embodiment, flow deflector sleeve 62C can be designed to revolve around chamber 58. This feature can be used to improve the uniformity of the refrigerant spray. In another embodiment, a focal spray of refrigerant will be rotated around the inside surface of the balloon. This has the effect to raise the average temperature of the therapy, compared to a continuous spray. This can be used to make a relatively 'colder' refrigerant such as nitrous oxide, which evaporates at about minus 90° C. at atmospheric pressure, mimic the effect of a 'warmer' refrigerant such as R-410a, which evaporates at about minus 50° C. at atmospheric pressure.

Figure 8:
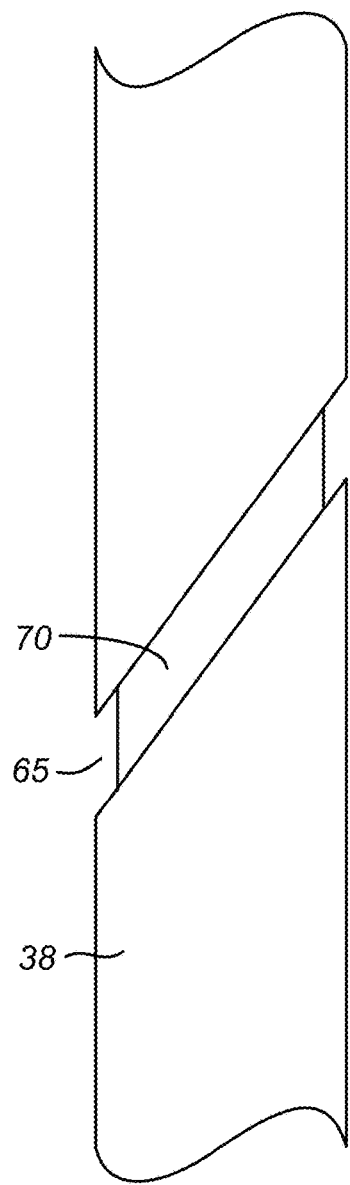
FIGS. 8, 9 and 10 are side views illustrating three different configurations of refrigerant delivery openings.
Figure 9:
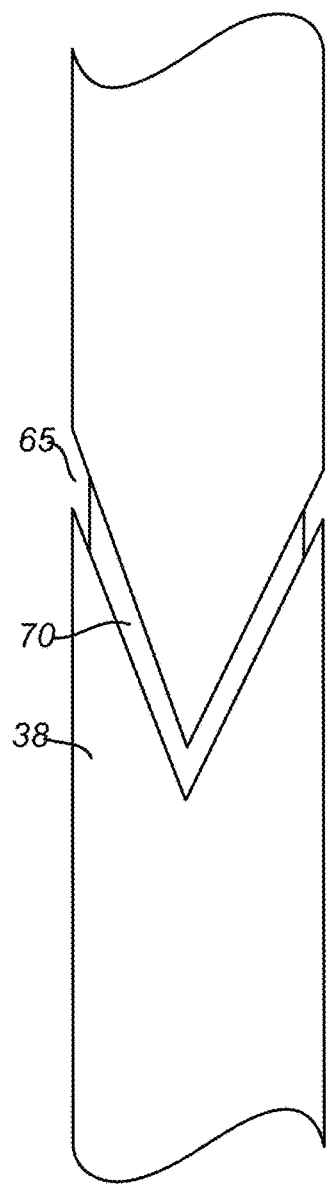
Figure 10:
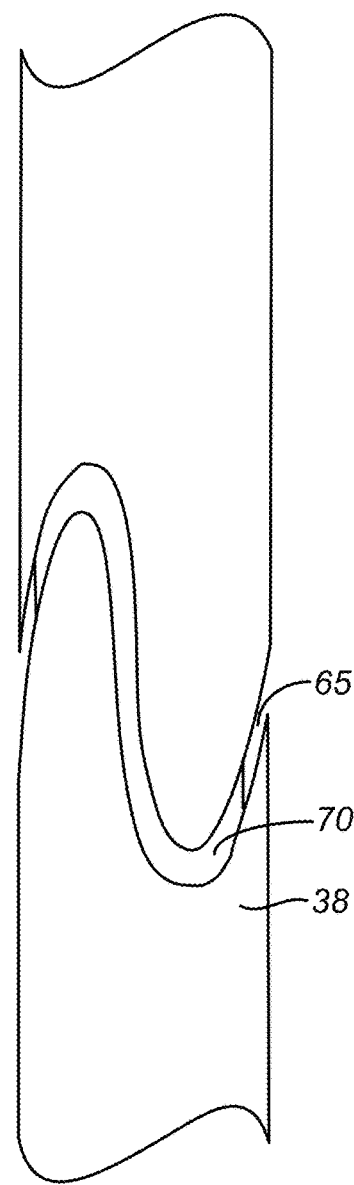

Full, 360° distribution of refrigerant 24 may not require that the gaps defining the refrigerant delivery openings, that is jets 65, be continuous. Also, the gaps defining jets 65 need not have a constant longitudinal or axial position. For example, FIG. 7 illustrates a variable width over the length of jets 65 and FIGS. 8-10 illustrate three different circumferential shapes of jets 65 that can be used to provide a degree of longitudinal spray to refrigerant 24. In particular, the refrigerant delivery opening 65 of FIG. 8 defines an oval path extending along the axis of tube 70 at an acute angle to the axis. In FIG. 9 the refrigerant delivery opening 65 defines a path having a series of generally straight segments extending along the axis at different acute angles to the axis with adjacent segments extending in opposite axial directions. FIG. 10 shows an example in which the refrigerant delivery opening 65 defines a path extending along the axis, the path having at least one and preferably at least two generally S-shaped curved segments.

Additional shapes and arrangements for the gaps defining jets 65, such as a series of circular holes and/or oblong slots, could also be used. Although a number of examples are described herein, the invention is not limited to the examples shown.

Figure 29:
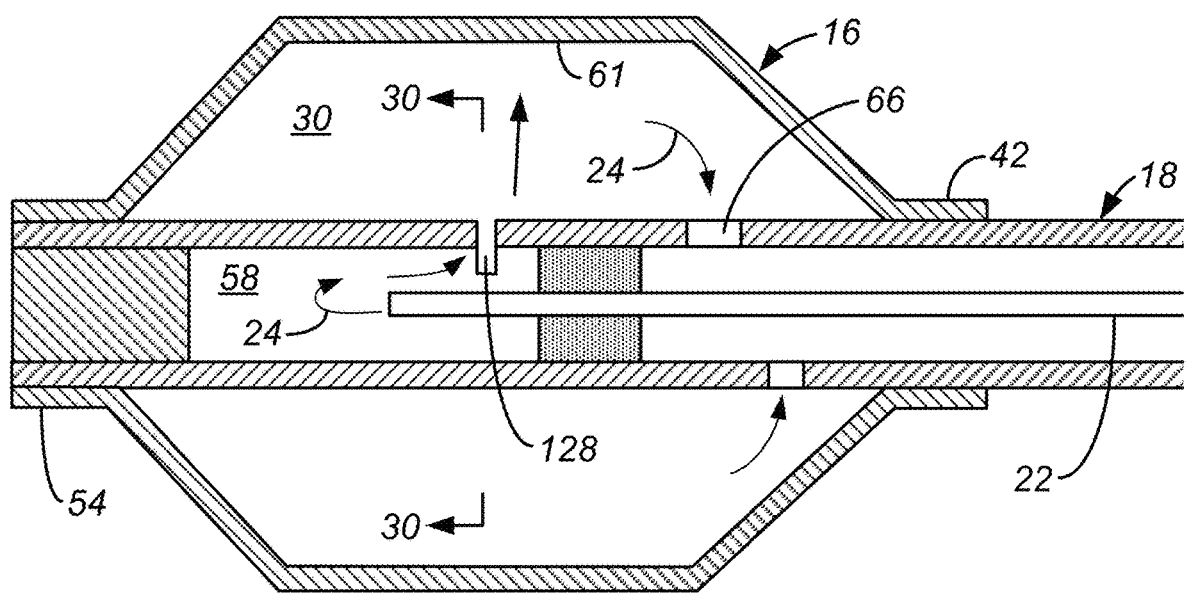
FIG. 29 is a side cross-sectional view of structure similar to that of FIG. 5 in which the refrigerant delivery nozzle is shaped to spray refrigerant over about 180° of the balloon.
Figure 30:
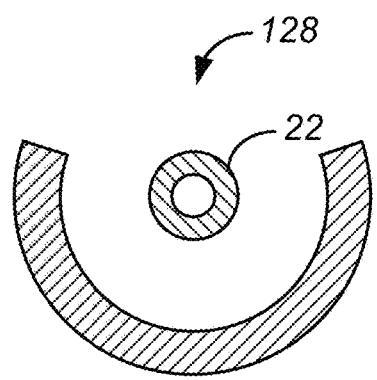
FIG. 30 is a cross-sectional view taken along line 30-30 of FIG. 29.

The examples so far discussed have all provided coverage over substantially 360°. By making the gaps defining jets 65 be more limited in scope, ablation over only a portion, such as about half or about one quarter, of the circumference can be achieved. In this case, it may be desirable to ablate only these portions of the esophagus. One embodiment of the invention for doing so is illustrated in FIGS. 29 and 30. In this device, the refrigerant flow is directed through a refrigerant delivery nozzle 128 into some portion of the circumference of balloon 16. As previously disclosed, significant heat transfer is only possible where the liquid refrigerant is evaporating on inner surface 61 of balloon 16. For example, the system could be designed to treat approximately ½ of the circumference, by designing the system to only spray refrigerant on approximately ½ of the circumference of the inside of the balloon as shown in FIGS. 29 and 30. In the case that full circumference treatment was desired, the user could perform a treatment and then rotate the catheter 180°. Alternatively, the user could choose to treat the untreated portion of the esophagus at some later date, e.g. 30 days later, as this may reduce the possible of undesirable complications, such as esophageal stricture. Refrigerant delivery nozzles 128 can be formed having greater or lesser spans of coverage. Also, refrigerant delivery nozzles 128 may not be continuous but could be two or more nozzle segments. Further, two or more refrigerant delivery nozzles 128 can be located at axially spaced apart positions.

Figure 31:
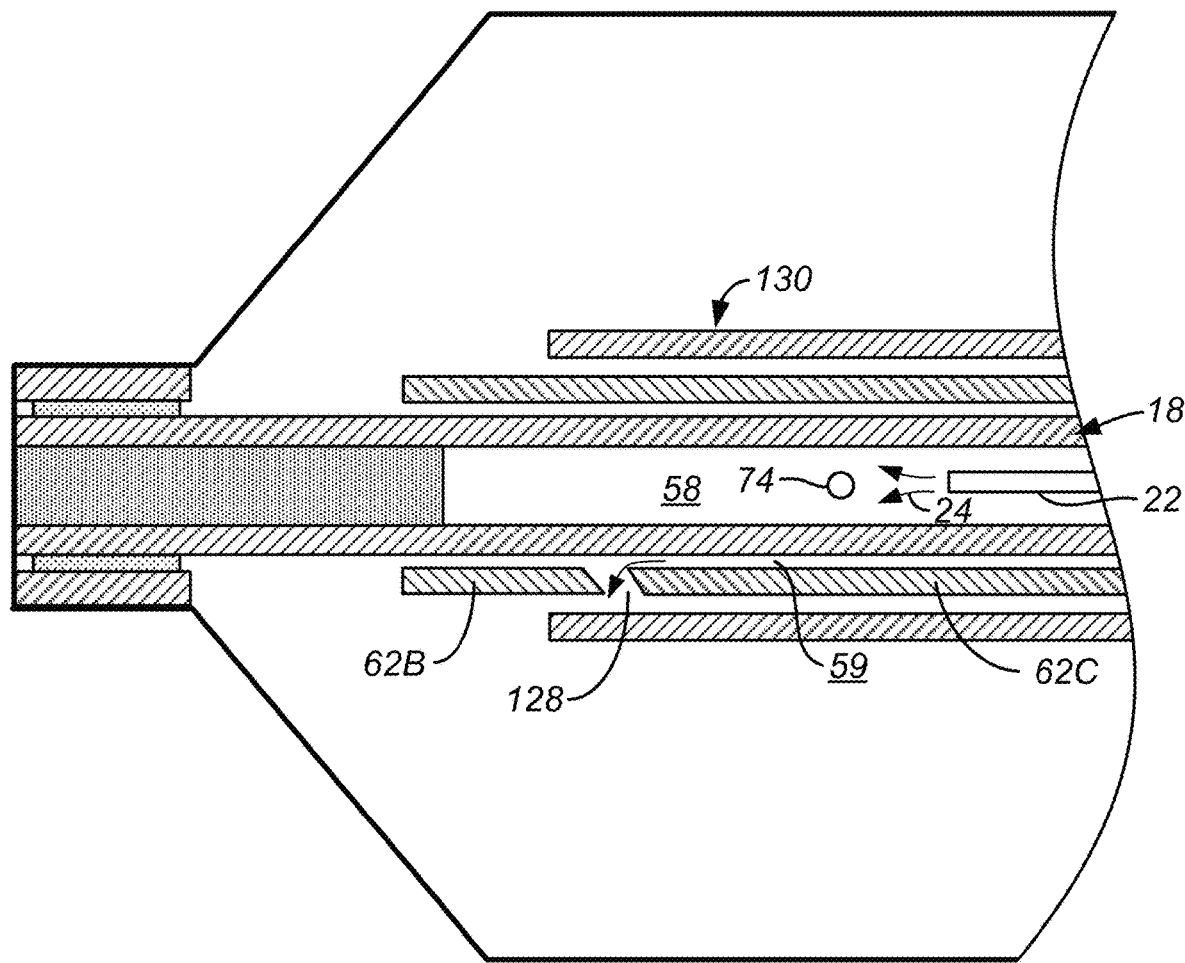
FIG. 31 is a simplified cross-sectional view of structure similar to that of FIG. 29 in which the refrigerant delivery nozzle extends completely around the circumference and is oriented at an angle to the axis, similar to that shown in FIG. 8, the structure having an axially positionable flow director sleeve used to permit selectively changing the circumferential extent of the refrigerant spray.
Figure 31A:
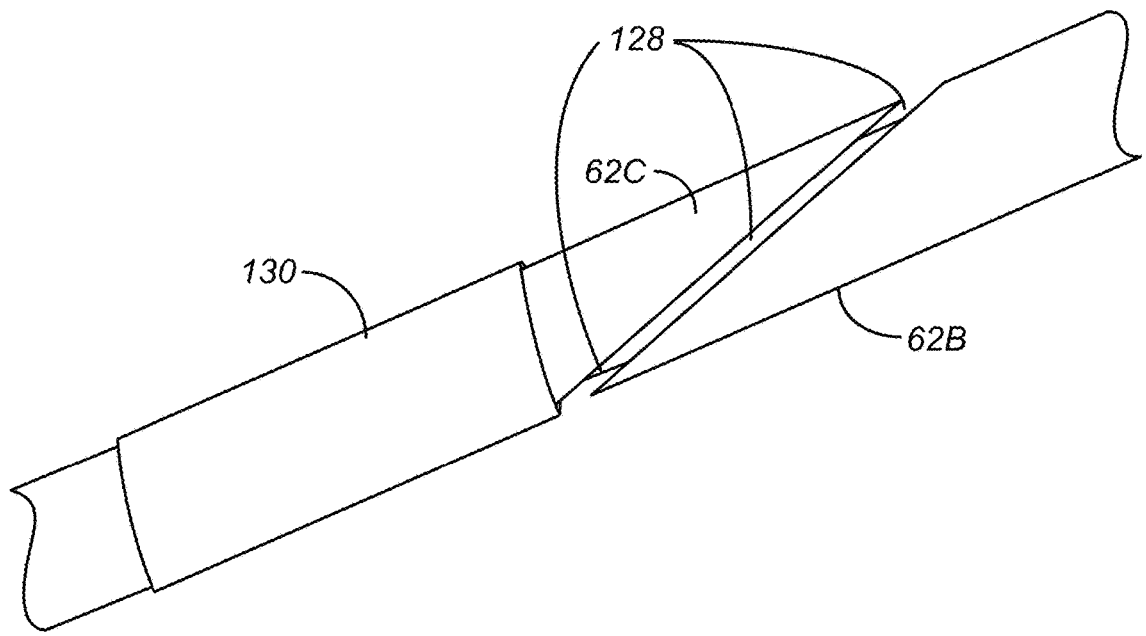
FIGS. 31A and 31B are simplified views illustrating how the structure of FIG. 31 can have the circumferential extent of the refrigerant spray varied between 0° and 360° by the axial movement of the flow director sleeve.
Figure 31B:
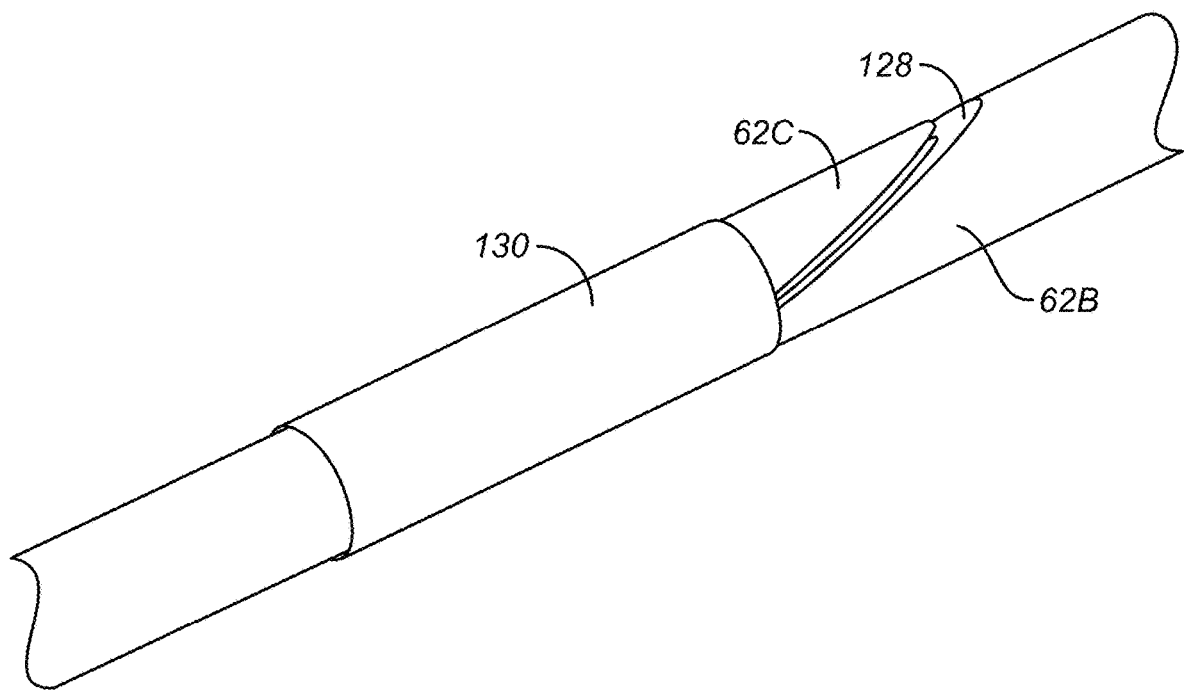
Figure 32:
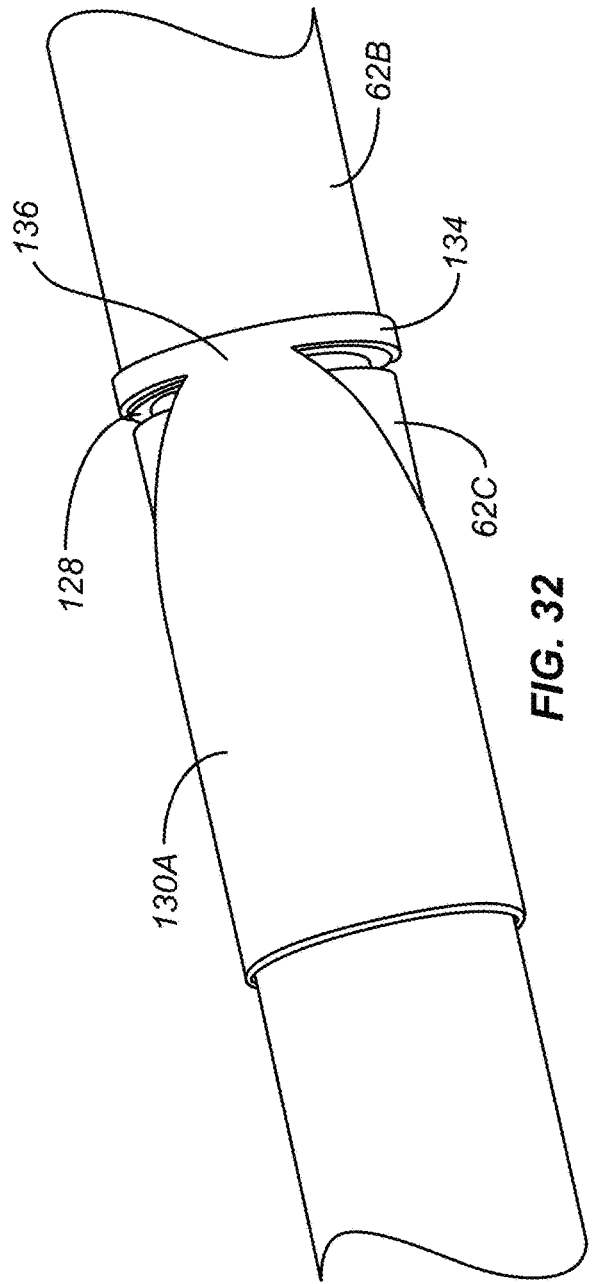
FIGS. 32, 32A and 32B show another configuration in which the refrigerant delivery nozzle is a full circumferential nozzle normal to the axis of the shaft with the flow director sleeve having an angled cut out so that the position of the flow director sleeve determined how much of the nozzle is exposed.
Figure 32A:
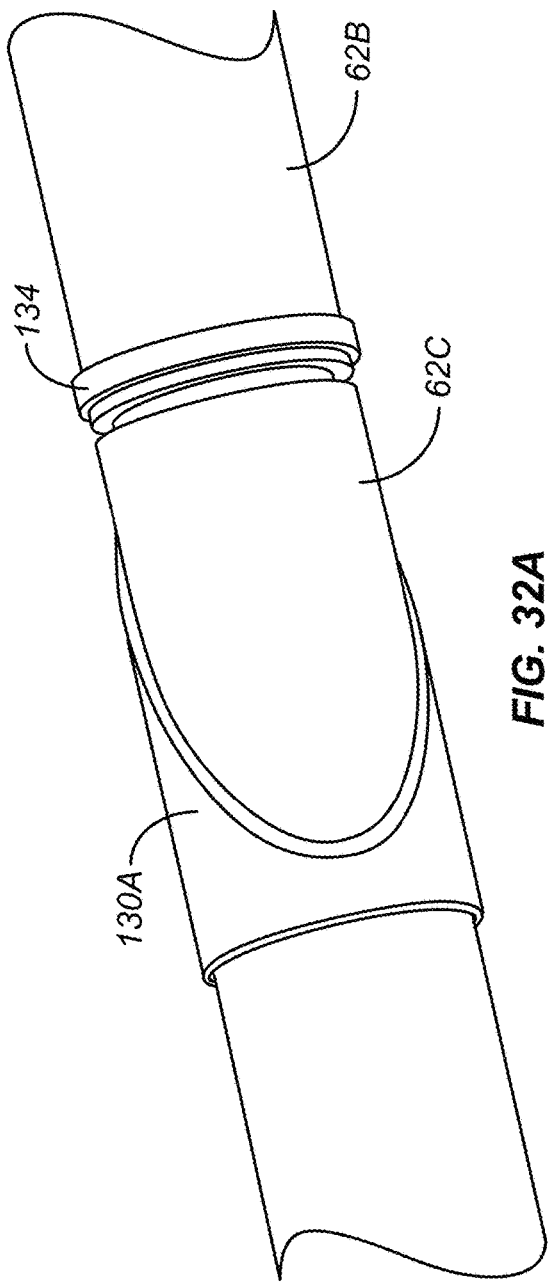
Figure 32B:
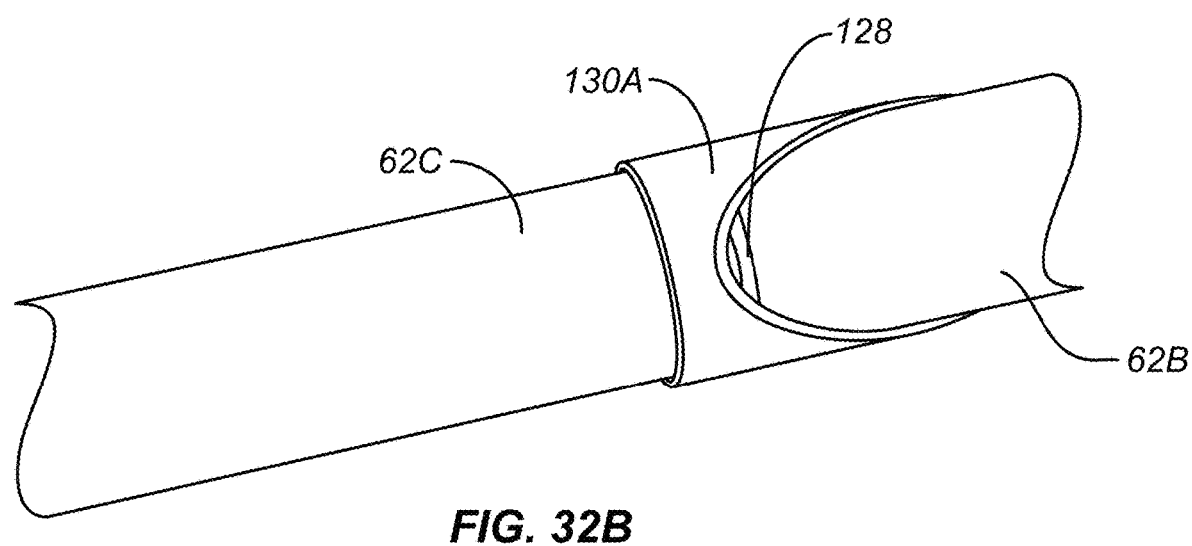
Figure 32C:
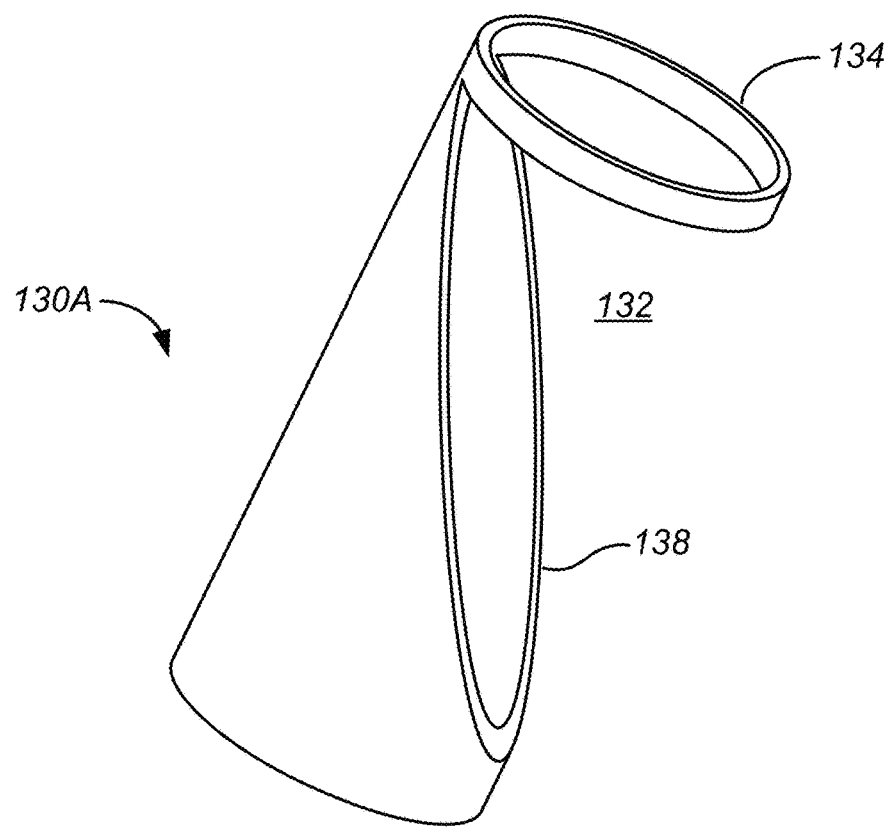
FIG. 32C is an overall view of the flow director sleeve of FIGS. 32, 32A and 32B.

In other embodiments, the device is able to selectively treat a variable circumference. In one configuration, see FIGS. 31-31B, refrigerant delivery nozzle 128 is a full circumference nozzle but is formed at an angle to the axis of shaft 18 as shown in FIGS. 8 and 31A. The axial position of a flow director sleeve 130 determines how much of nozzle 128 is exposed. In FIG. 31A entire nozzle 128 is exposed while in FIG. 31B about half of the nozzle is covered by sleeve 130. This permits the user to adjust the extent of the spray among a range of spray angles from 360° to essentially no spray. The flow director sleeve 130 can be connected to a wire which passes though shaft 18 to allow the user to control the axial position. In another configuration, see FIGS. 32-32C, refrigerant delivery nozzle 128 is a full circumference nozzle normal to the axis of shaft 18. Flow director sleeve 130A has a cutout region 132 leaving a stabilizing ring 134 at its distal end connected to the remainder of sleeve 132 at a junction 136. Cutout region 132 also defines a distally facing edge 138 arranged at an angle, such as 45°, to its axis. The axial position of a flow director sleeve 132 determines how much of nozzle 128 is exposed. In FIGS. 32 and 32A substantially the entire nozzle 128 is exposed so to permit delivering a refrigerant in substantially a full 360° pattern. In FIG. 32B, most of nozzle 128 is covered by sleeve 130A thereby delivering refrigerant over about ⅛ of the circumference.

Figure 11:
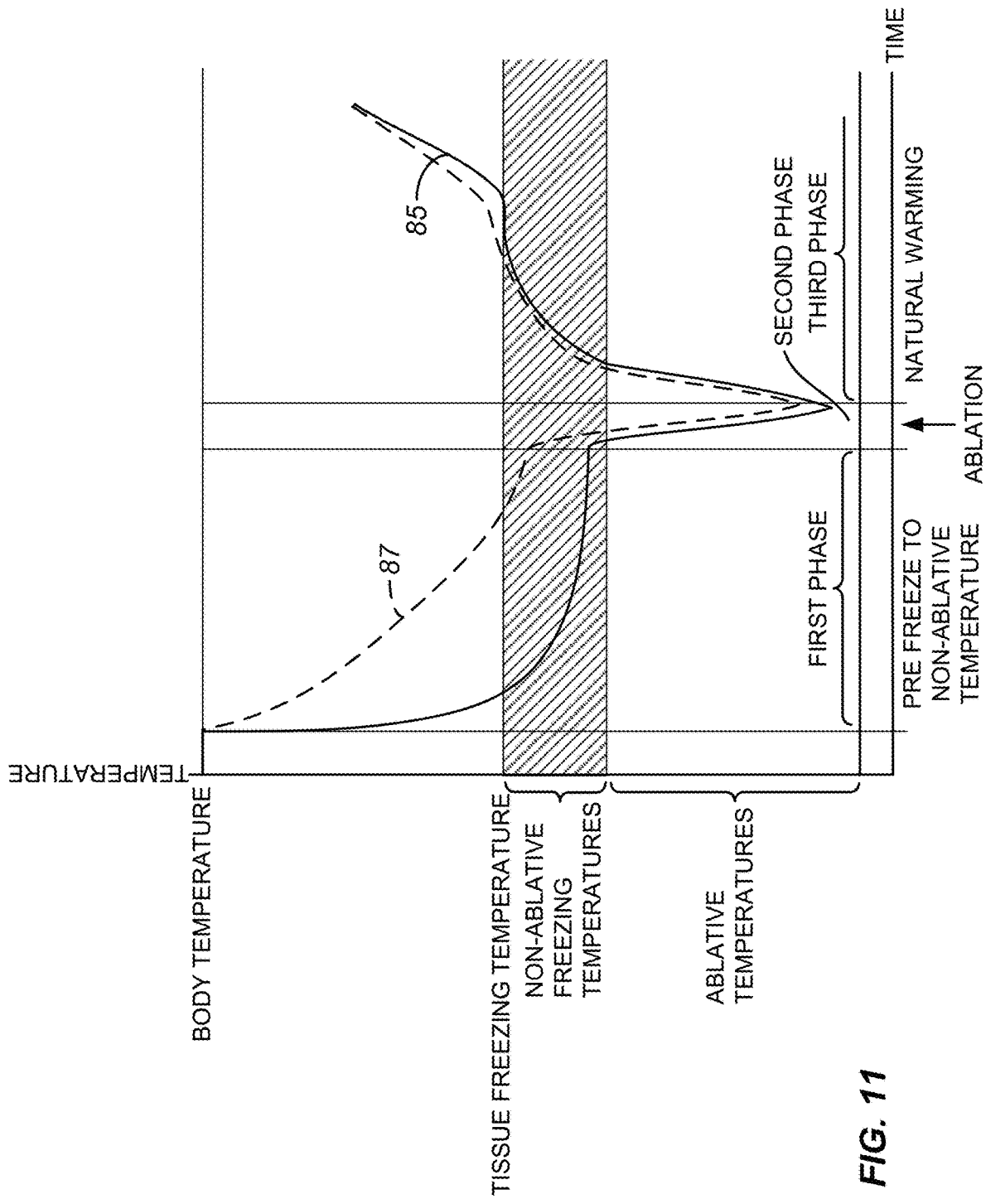
FIG. 11 shows a typical temperature curve during a procedure in which the target tissue is pre-chilled to non-ablative freezing temperatures followed by ablative freezing temperatures.

Typically, increasing treatment times will also improve the uniformity of the ablation. Long treatment times allow for more uniform surface cooling due to thermal conductivity of the lumen being treated; furthermore, longer treatment times are more likely to mitigate the somewhat random nature of refrigerant spray within the balloon (due to manufacturing variances, uncertainty associated with two phase refrigerant flow, etc). On the other hand, increasing treatment times generally results in a deeper effect than may be desired. Therefore it is desirable to protect the deeper tissues from the thermal insult when increasing the treatment times. For example, one way to increase treatment time is to pre-chill or pre-freeze the extracellular water in the target tissue to a non-lethal temperature (typically ~−10 to −2° C.) and then immediately drop the temperature to induce intracellular ice formation in the target tissue (~<−15° C.). FIG. 11 shows a typical temperature curve for this pre-chilling treatment. Solid line 85 is the balloon temperature at the point of most rapid cooling and dashed line 87 shows the slowest cooling rate of the balloon. During the first phase of treatment, the entire target tissue is cooled to non-ablative freezing temperatures. The duration of this first phase is such that the tissue in contact with the balloon area of slowest cooling freezes. This duration will not typically be 'actively' controlled, but rather experimentally determined by testing a wide range of catheters and statistically determining the ideal duration. During the second phase of treatment the balloon temperature is dropped rapidly to induce necrosis in the target tissue. The tissue can be cooled extremely rapidly during this phase as the energy requirements to reach necrosis inducing temperatures is much lower as much of the tissue is already frozen; furthermore, the specific heat capacity ($C_p$) of the frozen tissue is lower than the $C_p$ of normal tissue. Additionally, the tissue can be more uniformly cooled as the thermal conductivity of the frozen tissue is much higher than that of normal tissue. The third phase typically consists of the natural warming of the tissue.

A variety of means are available to induce this type of temperature gradient. It may be desirable to develop multiple temperature profile algorithms to treat to differing target treatment depths.

In one embodiment, the balloon pressure could be decreased at the time that the temperature drop was required. As the evaporation temperature of the refrigerant is directly related to the balloon temperature, this pressure drop will result in a temperature drop within the balloon. Ideally, the chosen refrigerant will have a fairly large temperature change relative to pressure as it is desirable to operate the balloon at pressures less than 1 atmosphere unless additional balloon diameter limiting features have been employed.

In another embodiment, multiple refrigerants can be used to create the variable temperature effect. In the example of FIG. 12, two refrigerant cylinders 34A and 34B are selectively connected to refrigerant delivery tube by valves 35A and 35B. During operating, refrigerant A (typically R134a, R422b, or similar) in cylinder 34A would first used for the warmer extracellular cooling/freezing temperature. Refrigerant B (typically R404, R410a, or nitrous oxide) in cylinder 34B would then be used to induce intracellular ice formation to achieve the desired damage to the tissue.

In other embodiments, the two refrigerants could be contained in a single cylinder. One method for accomplishing this is shown in FIG. 13. In this design, Refrigerant B, the lower temperature refrigerant, is placed into cylinder 34C followed by a divider/rupture disc 82. The divider/rupture disc 82 can be press-fit or the cylinder can be swaged to create a tight seal. The cylinder would then be kept at a sufficiently low temperature that prevents failure of the rupture disc. Refrigerant A, the higher temperature refrigerant, is then placed into cylinder 34C and an end cap 84 with a penetrable seal 86 is press-fit or swaged into the end of the cylinder. As the pressure of Refrigerant A is now acting on the opposite side of the rupture disk 82, the disk will not fail. During operation, seal 86 of cylinder 34C is punctured and the initial cooling is conducted with Refrigerant A. Once Refrigerant A has been fully consumed, the pressure in that portion of the chamber will fall, resulting in failure of rupture disk 82. Once rupture disk 82 has failed, Refrigerant B will be delivered to the balloon 16, completing the treatment.

It is also possible that the two refrigerants are insoluble in each other and the liquid phase of Refrigerant A is of higher density than the liquid phase of Refrigerant B. In this event, the two refrigerants could be placed in a cylinder without a divider/rupture disk 82.

Another technique to improve balloon surface temperature distribution is the addition of a heat transfer medium to the refrigerant. Although this has the net effect of reducing the absolute cooling power of the system, it functionally increases the heat transfer coefficient of the balloon. For example, a material such as silicone or mineral oil can be dissolved into the refrigerant at the time of bottling. Typically, the percentage (by volume) of oil would be 1-10%. Under normal operation (i.e. no added heat transfer medium), refrigerant exits the delivery side into the balloon at a temperature approximately equal to the delivery cylinder temperature. As the refrigerant exits the delivery side, the pressure of the refrigerant drops rapidly causing some evaporation and super-cooling of the remaining liquid refrigerant. The super-cooled liquid then strikes the balloon wall and evaporates, creating a gas barrier between the liquid refrigerant and the balloon wall. Therefore, by adding a non-volatile element to the liquid refrigerant, improved heat transfer will occur as the liquid refrigerant will also cool the heat transfer medium which will tend to adhere to the balloon surface.

Additionally, the refrigerant distribution may be aided by reducing the effect of refrigerant surface tension, which causes the refrigerant to flow as a sheet on the inside of the balloon. The surface tension of the refrigerant could be reduced by the addition of a surfactant such as sodium lauryl sulfate or polyethylene glycol to the refrigerant. In some cases the surfactant can be applied to the inner surface of the balloon.

Figure 14:
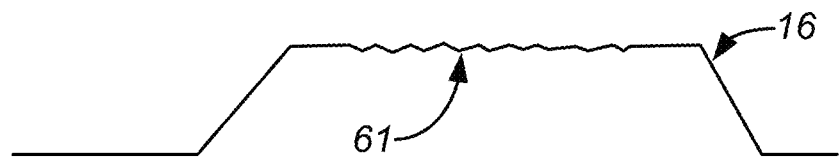
FIG. 14 is a simplified view showing how the inner surface of the balloon can be roughened by deforming the balloon wall to help cause the refrigerant to adhere to be balloon inner surface.
Figure 15:
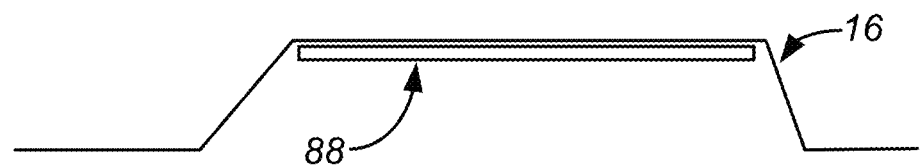
FIG. 15 shows the addition of a thin film of absorbent material to the inside surface of the balloon to help cause the refrigerant to collect against the inside surface of the balloon.

Another technique to mitigate the effect of surface tension is to alter the inner surface 61 of balloon 16 so that it is not a uniform surface. One technique, illustrated in FIG. 14, would be simply to roughen inner balloon surface 61. One way of doing so would be to deform the entire wall thickness as shown in FIG. 14. Roughening inner surface 61 could be accomplished by chemically or otherwise treating only inner surface 61 of balloon 16. Another way would be the addition of a thin film of absorbent material 88 to inside balloon surface 61 as shown in FIG. 15. That is, absorbent material 88 would tend to absorb the refrigerant to help keep the refrigerant adjacent to the inner balloon surface.

Figure 16:
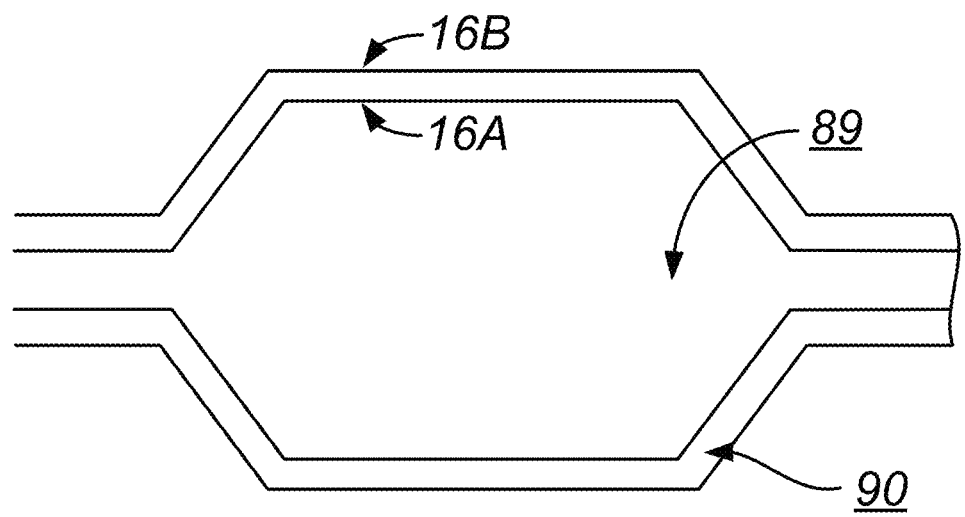
FIG. 16 illustrates inner and outer balloons defining an interstitial space within which the refrigerant can be filled.

In another embodiment, see FIG. 16, the refrigerant could be injected into an interstitial space 90 created by using inner and outer balloons 16A and 16B as shown in FIG. 16. As the volume of this space 90 is relatively small, the entire volume could be safely filled with liquid refrigerant, thereby creating a uniform surface temperature. The interior 89 of inner balloon 16A would typically be filled with a fluid such as air, which has low specific heat capacity and thermal conductivity.

It may be desirable to control the expansion of the balloon so as to prevent excessive force being applied to the esophagus while taking the native shape of the esophagus applying consistent ablation along the target treatment site. In such cases, it may be useful to exploit the pressure-diameter relationship of elastic balloons. In one embodiment, as shown in FIG. 17, a controlled balloon expansion assembly 91 comprises a relief valve assembly 93 and shaft 18. Shaft 18 is fluidly coupled to interior 30 of balloon 16. Relief valve assembly 93 includes a chamber 92 fluidly coupled to interior 46 of shaft 18. Relief valve assembly 93 also includes a syringe 96, or other user-controlled pressurization device, and valving, such as a control valve 98. Within chamber 92 is a bladder 94 which is in fluid communication with syringe 96. Control valve 98 controls flow from syringe 96 to both bladder 94 and shaft 18. A refrigerant delivery tube 22 is disposed within shaft 18. Refrigerant delivery tube 22 could be routed to balloon 16 separately from shaft 18; for example, the distal end of tube 22 could be passed into the end of balloon 16 opposite to where shaft 18 enters the balloon. Syringe 96 is typically filled with a gas such as air.

The control valve 98 is placed in position 1 of FIGS. 17 and 17A and bladder 94 and balloon 16 are pressurized with gas from syringe 96. A flow restriction device 100 is placed between control valve 98 and shaft 18 so that bladder 94 inflates at a faster rate than balloon 16 to prevent the gas from syringe 96 from escaping through an opening 101 in chamber 92 and into the ambient environment, or other exhaust gas dumping region. Under direct visualization, balloon 16 is inflated to the desired diameter. Once the desired diameter is achieved, control valve 98 is placed into position 2 of FIG. 17B so that no fluid flows through valve 98. Refrigerant flow through delivery tube 22 is initiated, passes into balloon 16 and then out of the balloon back through interior 46 of shaft 18 and into chamber 92. Once the pressure in chamber 92 exceeds the pressure in bladder 94, the bladder is sufficiently deformed allowing the exhaust refrigerant gas 124 to pass the bladder and exit to atmosphere through opening 101 in chamber 92 thereby regulating balloon pressure (and therefore balloon diameter) to a pressure slightly greater than the pressure in the bladder. Once treatment is complete, the control valve is placed in position 3 of FIG. 17C to allow evacuation of and thus deflation of balloon 16 with exhaust gas 124 passing into syringe 96. As bladder 94 is still inflated, the balloon can hold vacuum and thus be completely collapsed through the use of syringe 96; this helps to facilitate removal of the balloon from the endoscope (not shown) or other placement device. The use of syringe 96 instead of some other type of pressurization device provides the advantage of using one device to both pressurized bladder 94 and to create a suction force to help collapse balloon 16. If another treatment is desired, the control valve can be placed into position 1 of FIG. 17A and the process can begin again. If desired, bladder 94 can be independently inflated and deflated by placing valve 98 into position 4 of FIG. 17D.

In some examples valve 98 can be replaced by two valves, each coupled to syringe 96 with one valve coupled to bladder 94 and the other valve coupled to interior 46 of shaft 18, typically through flow restriction device 100. In some examples bladder 94 can be replaced by a different type of pressure sensitive sealing element. For example, bladder 94 could be replaced by a piston and cylinder arrangement fluidly coupled to control valve 98 and used to operate a flapper valve within chamber 92; when a sufficient pressure within interior 46 of shaft 18 was achieved, the pressure would cause the flapper valve to open sufficiently permit the passage of the exhaust valve on 24 past the flapper valve and out through opening 101.

Figure 17E:
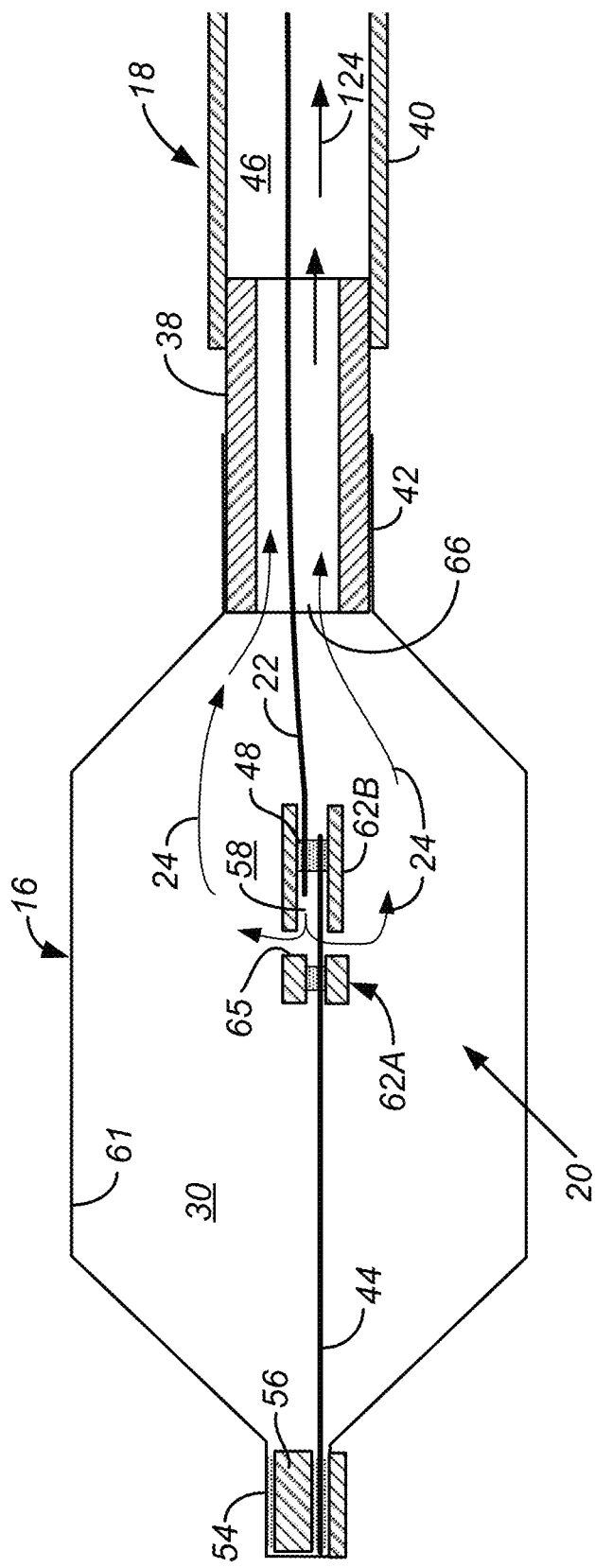
FIG. 17E illustrates apparatus similar to that of FIG. 5 but without the exhaust sleeve to reduce the restriction to the flow of the exhaust gases.

In embodiments with highly compliant balloons, the balloon pressure may need to be much lower than 10-psig. In these cases, maximizing the size of the exhaust lumen is necessary. Typically, the smallest hydraulic diameter is in the area of the proximal end 42 of balloon 16. As shown in FIG. 17E, this diameter can be maximized by having only refrigerant delivery tube 22 pass through this area. In order to achieve the longitudinal stiffness required for passage thru the endoscope, refrigerant delivery tube 22 would typically be constructed from a stainless steel hypotube. Alternatively, the delivery tube could be a plastic such as polyimide, and a metal support wire could pass through the length of the catheter. Rigid refrigerant delivery tube 22 also provides longitudinal stiffness for balloon 16.

Figure 17F:
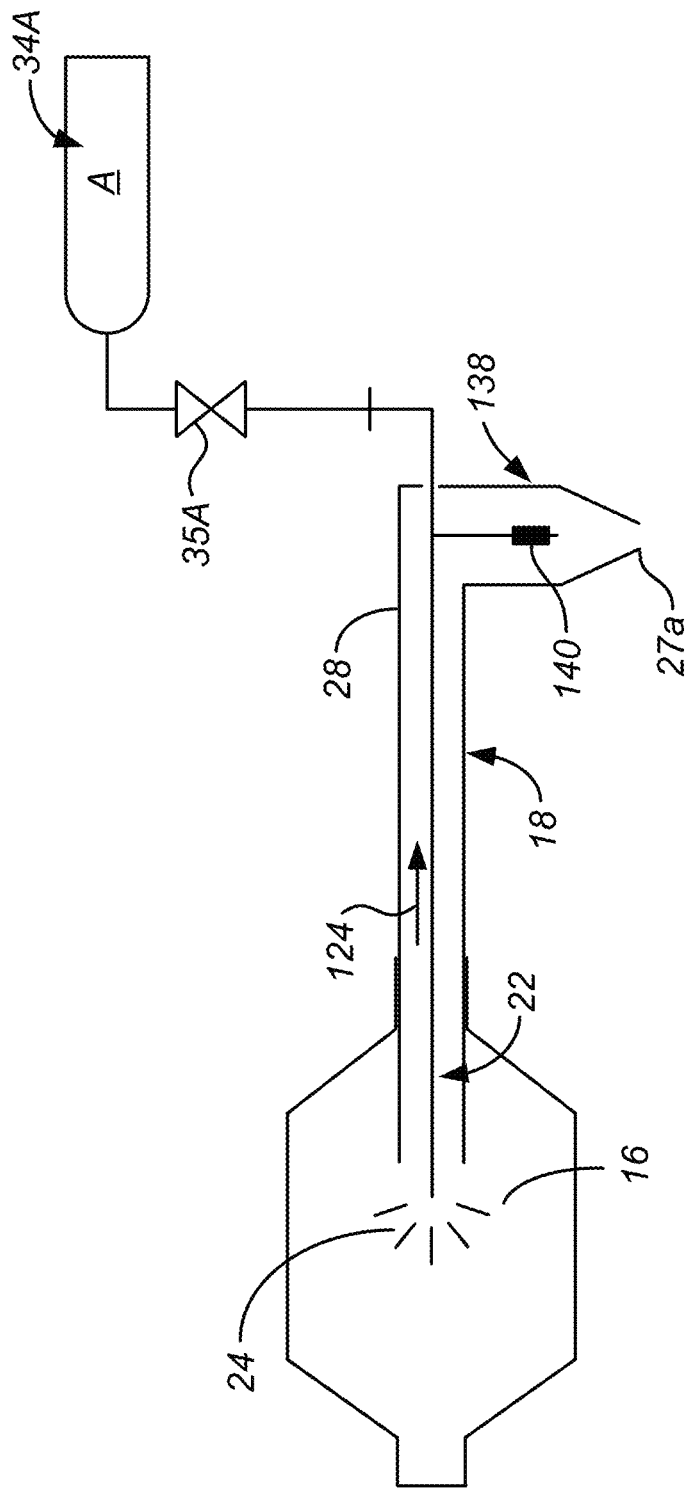
FIG. 17F shows another technique for reducing balloon pressure by creating a lower pressure at the exit port.

In other cases, the balloon pressure can be lowered by connecting the proximal end 28 of shaft 18 to a suction source in the procedure room. Alternatively, the vacuum could be created by the integrating a Venturi vacuum generator 138 into the device as shown in FIG. 17F. Generator 138 includes a nozzle 140 connected to refrigerant delivery tube 22. High-pressure refrigerant flows from nozzle 140 through a constricting exit port 27a. This creates a lower pressure at exit port 27a helping to pull exhaust gas stream 124 through shaft 18 and out of the shaft through exit port 27a.

Additionally, exploiting the glass transition temperature (Tg) of the balloon material is also useful to preventing over-dilatation of the esophagus. For example, the balloon is statically inflated to the desired size and the refrigerant flow is then initiated. Due to the low thermal mass of the balloon, virtually instantaneous cooling is achieved and due to the glass transition temperature of the material being higher than the refrigerant evaporative temperature, the modulus of the balloon increases dramatically causing the balloon to be stretch-resistant. As a result, further expansion of the balloon is prevented. Therefore, it is desirable to select a polymer that has low modulus so that it is stretchy at normal body temperatures (~37° C.), and high modulus so that it is stretch-resistant at the target therapeutic ablation temperature, sometimes called the target tissue treatment temperature range (typically within the range of −15 to −90° C.). Many materials are available to meet this objective and can be blended to achieve the ideal glass transition temperature. For example, polyurethane has a Tg in the range of −10 to −50° C. commonly depending on the hardness (durometer rating) and a blend could be developed to be compatible with HFC type refrigerants. Other possible materials include low durometer PEBAX (Tg~−60° C.), low durometer polyethylene (~−100° C.), and silicone (~−130° C.). For example, a suitable target tissue treatment temperature range for a particular procedure may be −30 to −60° C. so that the material having a glass transition temperature of −50° C. would likely be a suitable choice.

As there are potential failure modes that could cause patient injury, it may be necessary to mitigate these risks in some fashion. One cause of concern is leaks. As the procedure is done under direct visualization, balloon rupture is likely to be quite easily detected. However, a leak that occurs distally of the inflated balloon could cause inflation and dilatation of the esophagus and stomach, possibly resulting in perforation before the leak is discovered. One cause of this type of leak would be a failure of the distal balloon joint at the distal end 54 of balloon 16. As a result, prevention and mitigation of this failure mode would be advantageous.

Thermally bonding the balloon 16 to the support structure, such as sleeve 56, may be preferred as this method typically results in the highest strength and is therefore the less likely to fail compared with a method such bonding with adhesive. Also, reinforcing the joint with a non-compliant material such as polyimide or PET can also significantly reduce joint failure.

Figure 18:
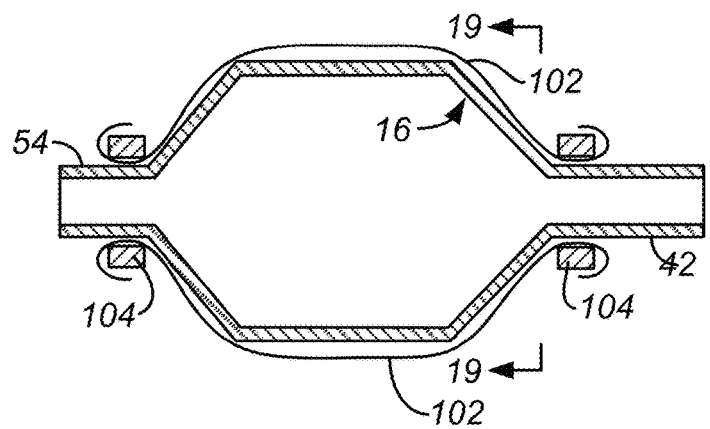
FIGS. 18 and 19 are cross-sectional and end views of an example of a balloon in which longitudinally extending filaments are used to create a containment cage for the balloon to help restrict excessive radial expansion.
Figure 19:
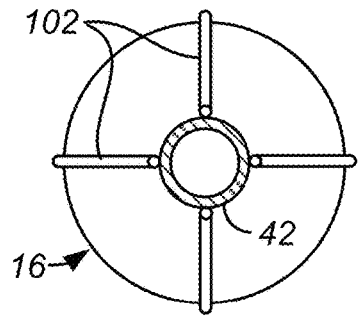

Additionally, reducing compliance (that is, expansion) in the longitudinal direction will also reduce the stress on the joint. One way to do so is by attaching high tensile strength filaments or strips 102 to balloon 16 as shown in FIGS. 18 and 19. Doing so creates a containment cage is created by the use of high tenacity polymer yarns such as Spectra or Zylon. The yarns can be mechanically attached to the balloon stem reinforcing bands 104. Typically 3-8 yarns are required.

Figure 20:
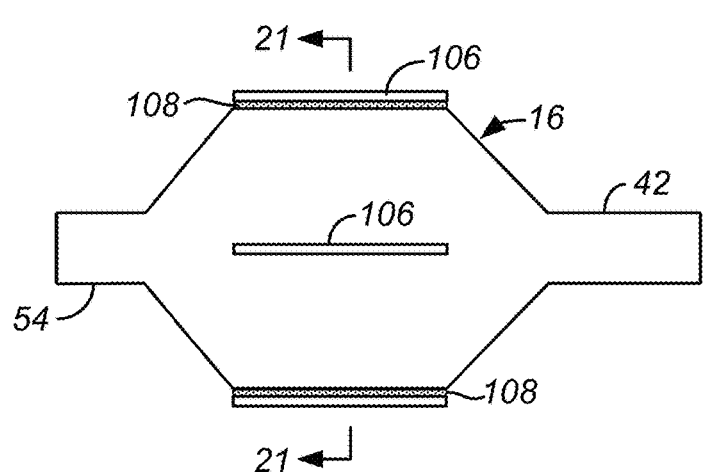
FIGS. 20 and 21 are simplified side and end views showing the use of non-compliant strips or wires bonded to the balloon for reinforcement.
Figure 21:
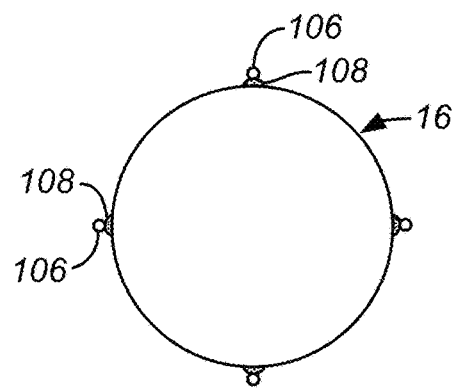

In another embodiment the balloon can be reinforced by attaching non-compliant strips or wires 106 to the balloon as shown in FIGS. 20 and 21. Preferably the strips would be constructed from a high strength thin film polymer such as PET or polyimide. The strips could be attached with a high strength adhesive 108 such as epoxy.

Alternately, as shown in FIG. 22, balloon 16 could be reinforced with an application of a high strength adhesive 110 as shown in FIG. 22. The adhesive could be applied in any combination of longitudinal and circumferential directions to achieve the desired reinforcement.

In another embodiment, see FIGS. 23 and 24, balloon 16 could be blown such that the wall had thicker portions 112 as shown in FIGS. 23 and 24. The location and orientation of the thicker portions can be adjusted according to how the expansion of balloon 16 is to be restricted. For example, thicker portions 112 can be formed as longitudinally extending portions, circumferentially extending portions, spirally extending portions, or portions extending in some other manner. One method of manufacture for longitudinally extending portions is to extrude the base tubing for the balloon as shown in FIG. 23 and then blow the balloon in a mold. If spirally extending portions are desired, the base balloon tubing can be twisted as it is drawn off of the extruder. Alternatively, the balloons could be manufactured from several components. For example, the longitudinal stiffening elements could be extruded independently of the base balloon tubing and then thermally bonded during the balloon blowing process.

It is also possible to reduce the longitudinal stress by attaching balloon 16 to shaft 18 so that distance between the ends 42, 54 of the balloon is shorter than the actual length of the balloon.

Figure 25:
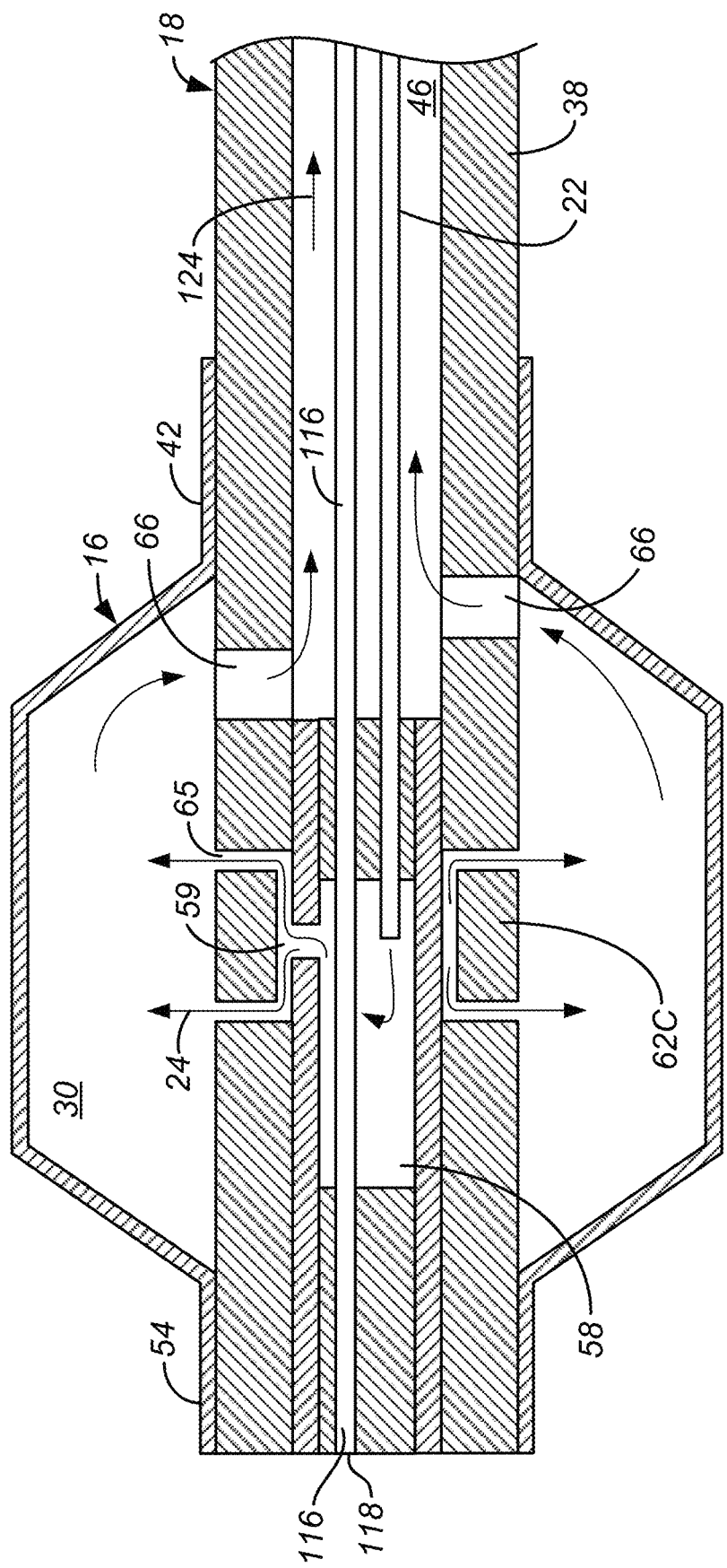
FIG. 25 shows structure similar to that of FIG. 6 but also including a pressure detection lumen having an opening at its tip to monitor the pressure within the hollow body structure distal of the balloon so to permit detection of a leak.
Figure 26:
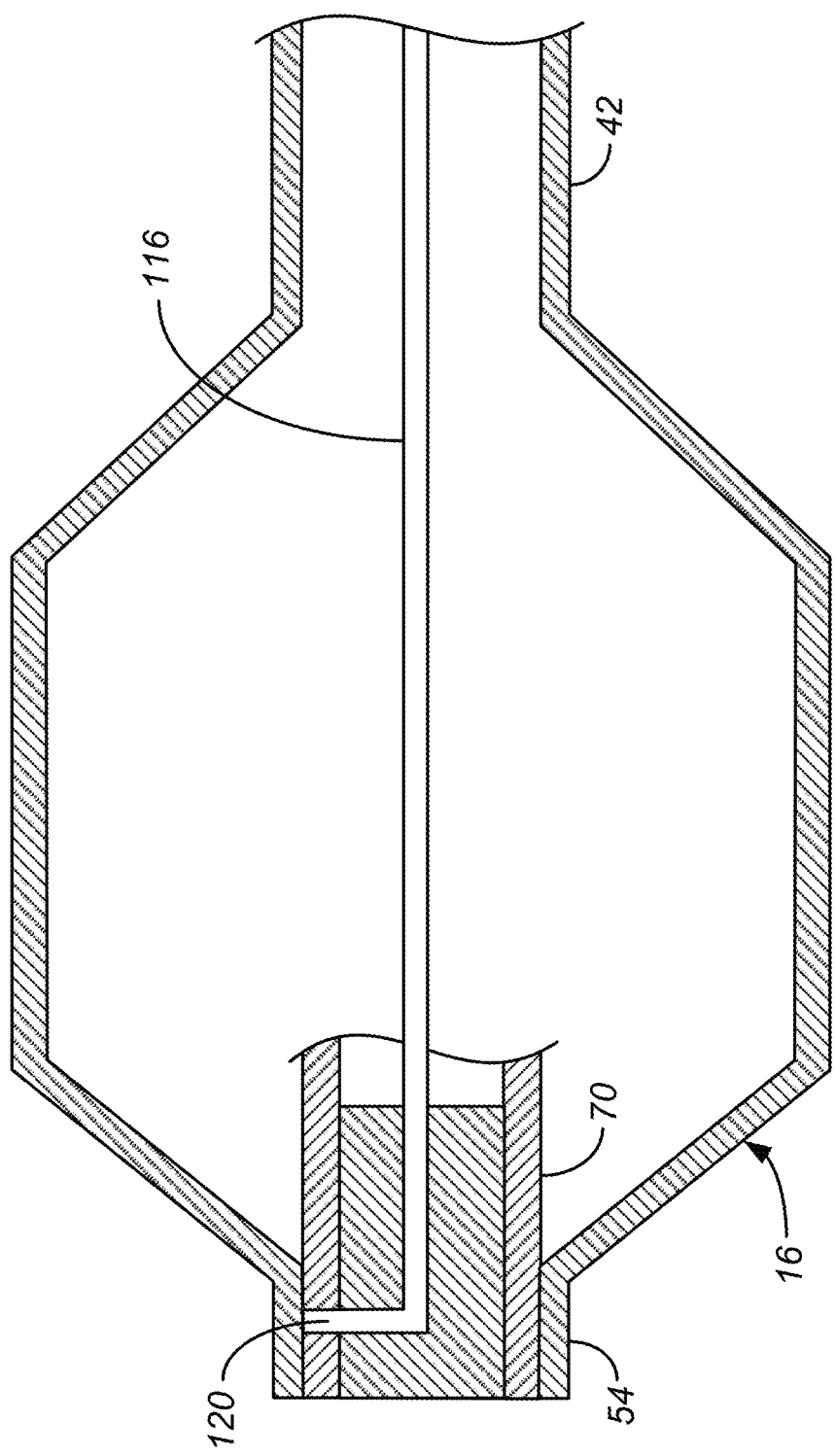
FIG. 26 shows a structure similar to that of FIG. 25 in which the flow detection lumen terminates at a cross hole formed at the joint between the distal end of the balloon and support structure so the failure of the joint will create a sudden change in pressure within the lumen.

Additionally, detection of a joint failure, either separately or in addition to automatic cessation of the refrigerant flow as is accomplished with the example of FIG. 17, is beneficial. One way to detect a leak is to measure pressure distal to the balloon. In one embodiment, as shown in FIG. 25, a pressure detection lumen 116 runs the entire length of the catheter assembly 12 and is open at its distal tip 118. The proximal end is tightly sealed and in fluid communication with a pressure sensing device, not shown, such as a pressure transducer. To effectively mitigate damage to the esophagus and stomach, detecting pressure changes of less than 1-psig than would necessary. Furthermore, due to the low threshold detection pressure, a filtering algorithm may be required to reduce false positives due to esophageal motility and eructation. Alternatively, the pressure in lumen 116 could be connected to a pneumatic actuator to directly terminate the refrigerant flow. In another embodiment, shown in FIG. 26, flow detection lumen 116 terminates under distal end 54 of balloon 16 at a cross-hole 120 formed through tube 70. In the event that the bond between balloon 16 and tube 70 fails so that balloon 16 separates from tube 70, gas is delivered into cross-hole 120 and through lumen 116. The sudden change in pressure within lumen 116 should be readily detectable.

Figure 27:
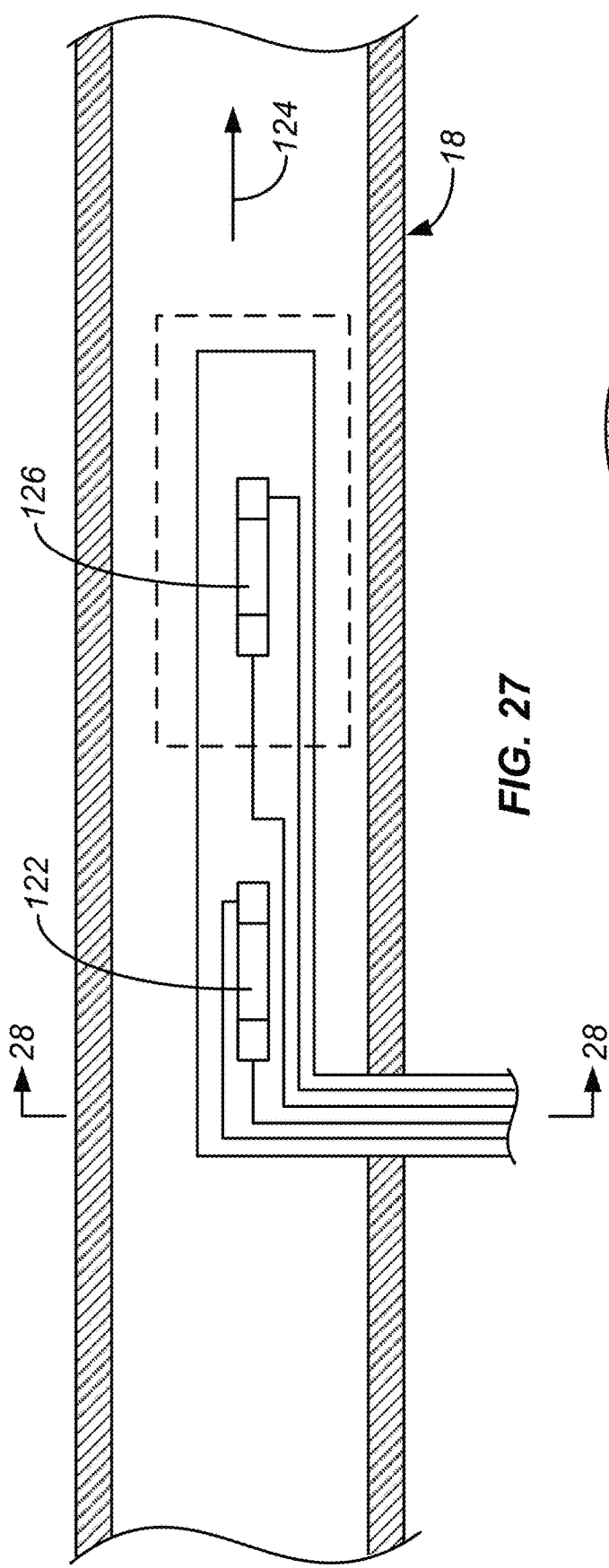
FIGS. 27 and 28 are side cross-sectional and end cross-sectional views of a portion of a placement catheter including a thermo resistive element placed along the exhaust gas stream to permit detection of a leak by monitoring for a drop in flow rate.
Figure 28:
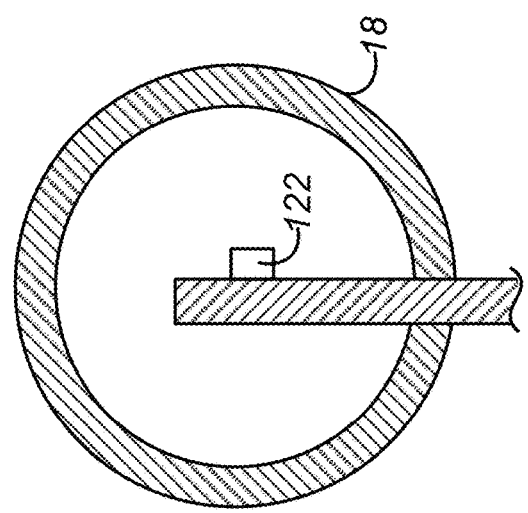

Another technique to detect a leak is to measure flow of the exhaust gas and terminate the flow of refrigerant in the event of a sudden drop in flow. One method of flow detection is shown in FIGS. 27 and 28. In this design, a low resistance (<1000 ohms, typically ~100 ohms) thermoresistive element 122 is placed into the exhaust gas stream 124. The thermoresistive element 122 is typically placed in series with a resistor in a typical voltage divider circuit, not shown. Once refrigerant flow is initiated, voltage is applied to the circuit (<12 VDC, typically 5 VDC) which causes the thermoresistive element 122 to heat. The exhaust gas stream 124 flowing past thermoresistive element 122 removes heat from element 122 at some rate proportional to the flow rate. The temperature of element 122 can be determined by measuring the voltage drop across the element. During use, a rise in the temperature of element 122 would indicate a drop in the flow rate and thus a potential leak.

If greater accuracy is required, a temperature sensing element 126 could be added to the circuit to reduce false-positives due to variations in exhaust gas temperature. Other methods of flow measurement such as measuring the pressure drop across some fixed length of the exhaust gas stream 124 could also be utilized.

The above descriptions may have used terms such as above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims.

Any and all patents, patent applications and printed publications referred to above are incorporated by reference.

What is claimed is:

1. A method for cryogenically treating esophageal target tissue at a target site, the method comprising:
    positioning a cryogenically-coolable balloon at the target site for cryogenic treatment of the esophageal target tissue, the cryogenically-coolable balloon having an inner surface, and the cryogenically-coolable balloon being made of balloon material having temperature-dependent elastic properties and stretch-resistant properties; and
    inflating the cryogenically-coolable balloon to a desired size, followed by:
    cooling the inner surface of the cryogenically-coolable balloon to a temperature that transitions the cryogenically-coolable balloon from having the elastic properties to having the stretch-resistant properties to prevent further expansion of the cryogenically-coolable balloon material while cryogenically treating target tissue at the target site.

2. The method according to claim 1,
    further including cooling the inner surface of the cryogenically-coolable balloon by delivering a refrigerant into the cryogenically-coolable balloon,
    wherein the refrigerant is a liquid refrigerant.

3. The method according to claim 1, further including:
    cooling the inner surface of the cryogenically-coolable balloon by delivering a refrigerant into the cryogenically-coolable balloon interior utilizing a refrigerant delivery device comprising:
        a flow deflector tube inside the cryogenically-coolable balloon;
        a circumferentially-extending refrigerant delivery opening formed in the flow deflector tube and fluidly coupled to the cryogenically-coolable balloon interior; and
        an axially-positionable flow director sleeve at least partially surrounding the flow deflector tube; and
    positioning the flow director sleeve to cover part or none of the circumferentially-extending refrigerant delivery opening thereby changing how much of the circumferentially-extending refrigerant delivery opening is exposed to adjust a circumferential extent of a spray of a refrigerant through the circumferentially-extending refrigerant delivery opening.

4. The method according to claim 3, wherein the refrigerant delivery opening extends along a path having changing rotary and axial positions.

5. The method according to claim 4,
    further including using a catheter having a catheter axis to position the cryogenically-coolable balloon at the target site,
    wherein the refrigerant delivery opening is a full circumference opening extending at an angle to the catheter axis.

6. The method according to claim 5, wherein the flow director sleeve is cylindrical.

7. The method according to claim 3, wherein the refrigerant delivery opening extends along a path having a constant axial position.

8. The method according to claim 7,
    further including using a catheter having a catheter axis to position the cryogenically-coolable balloon at the target site,
    wherein the flow director sleeve has first and second edges, the first edge arranged at an angle to the catheter axis.

9. The method according to claim 8, wherein the first edge is arranged at an angle of 45° to the catheter axis.

10. A system for cryogenically treating esophageal target tissue at a target site, the system comprising:
    a cryogenically-coolable balloon configured to be positioned at the target site for cryogenic treatment of the esophageal target tissue, the cryogenically-coolable balloon comprising an inner surface and being made of balloon material having temperature-dependent elastic properties and stretch-resistant properties,
    wherein the cryogenically-coolable balloon is configured to be:
        inflated to a desired size, and then;
        have the inner surface cooled to a temperature that transitions the cryogenically-coolable balloon from having the elastic properties to having the stretch-resistant properties to prevent further expansion of the cryogenically-coolable balloon material while cryogenically treating target tissue at the target site.

11. The system according to claim 10,
    wherein the inner surface of the cryogenically-coolable balloon is configured to be cooled by delivering a refrigerant into the cryogenically-coolable balloon, and
    wherein the refrigerant is a liquid refrigerant.

12. The system according to claim 10, further including:
    a refrigerant delivery device comprising:

a flow deflector tube inside the cryogenically-coolable balloon;

a circumferentially-extending refrigerant delivery opening formed in the flow deflector tube and fluidly coupled to the cryogenically-coolable balloon interior; and an axially-positionable flow director sleeve at least partially surrounding the flow deflector tube, wherein the inner surface of the cryogenically-coolable balloon is configured to be cooled by a refrigerant that is delivered into the cryogenically-coolable balloon interior using the refrigerant delivery device, and wherein the flow director sleeve is configured to cover part or none of the circumferentially-extending refrigerant delivery opening thereby changing how much of the circumferentially-extending refrigerant delivery opening is exposed to adjust a circumferential extent of a spray of a refrigerant through the circumferentially-extending refrigerant delivery opening.

13. The system according to claim 12, wherein the refrigerant delivery opening extends along a path having changing rotary and axial positions.

14. The system according to claim 13, further including a catheter having a catheter axis configured to position the cryogenically-coolable balloon at the target site, wherein the refrigerant delivery opening is a full circumference opening extending at an angle to the catheter axis.

15. The system according to claim 14, wherein the flow director sleeve is cylindrical.

16. The system according to claim 12, wherein the refrigerant delivery opening extends along a path having a constant axial position.

17. The system according to claim 16, further including a catheter having a catheter axis configured to position the cryogenically-coolable balloon at the target site, and wherein the flow director sleeve includes first and second edges, the first edge arranged at an angle to the catheter axis.

18. The system according to claim 17, wherein the first edge is arranged at an angle of 45° to the catheter axis.

* * * * *